(12) United States Patent
Gagnon et al.

(10) Patent No.: US 10,118,111 B2
(45) Date of Patent: Nov. 6, 2018

(54) APPARATUS, SYSTEM, AND METHOD FOR REMOVING GAS IN AN IMMERSION ULTRASONIC PROCESS

(71) Applicant: The Boeing Company, Chicago, IL (US)

(72) Inventors: Roy M. Gagnon, Summerville, SC (US); Jeffry J. Garvey, Charleston, SC (US)

(73) Assignee: The Boeing Company, Chicago, IL (US)

( * ) Notice: Subject to any disclaimer, the term of this patent is extended or adjusted under 35 U.S.C. 154(b) by 185 days.

(21) Appl. No.: 15/236,435

(22) Filed: Aug. 13, 2016

(65) Prior Publication Data

US 2018/0043285 A1   Feb. 15, 2018

(51) Int. Cl.
| | | |
|---|---|---|
| *B01D 19/00* | (2006.01) | |
| *G01N 29/28* | (2006.01) | |
| *G01N 29/22* | (2006.01) | |
| *G01N 29/265* | (2006.01) | |
| *G01N 29/32* | (2006.01) | |
| *G10K 11/00* | (2006.01) | |

(52) U.S. Cl.
CPC ..... *B01D 19/0078* (2013.01); *B01D 19/0094* (2013.01); *G01N 29/225* (2013.01); *G01N 29/265* (2013.01); *G01N 29/28* (2013.01); *G01N 29/32* (2013.01); *G10K 11/006* (2013.01); *G01N 2291/2694* (2013.01)

(58) Field of Classification Search
CPC .. B01D 19/00–19/0495; G01N 29/223; G01N 29/225; G01N 29/226; G01N 29/265; G01N 29/28; G01N 29/32; G01N 2291/2694; G10K 11/006
USPC ............. 73/584–648; 95/30, 241–266; 96/155–220
See application file for complete search history.

(56) References Cited

U.S. PATENT DOCUMENTS

| | | | |
|---|---|---|---|
| 6,210,470 B1 * | 4/2001 | Philips ............... | B01D 19/0078 95/30 |
| 7,285,096 B2 | 10/2007 | Burba et al. | |
| 7,628,075 B2 | 12/2009 | Kennedy et al. | |

* cited by examiner

*Primary Examiner* — T. Bennett McKenzie

(57) ABSTRACT

An apparatus for removing a gas in an immersion ultrasonic process is provided. The apparatus, in the form of an immersion ultrasonic transducer holder apparatus, has a body with a first end, a second end, a plurality of sides, and a hollow interior cavity portion. A holder portion with an exterior end and an interior end is formed through the first end, and holds one or more immersion ultrasonic transducers. A sloped inner face having a base end with a knife-edged perimeter is adjacent the interior end of the holder portion. The sloped inner face has an upward sloped surface extending from the base end to an evacuation end. One or more evacuation ports are formed through the first end, and adjacent the evacuation end. When the apparatus is used in the immersion ultrasonic process, the knife-edged perimeter, sloped inner face, and evacuation ports facilitate removal of the gas.

20 Claims, 11 Drawing Sheets

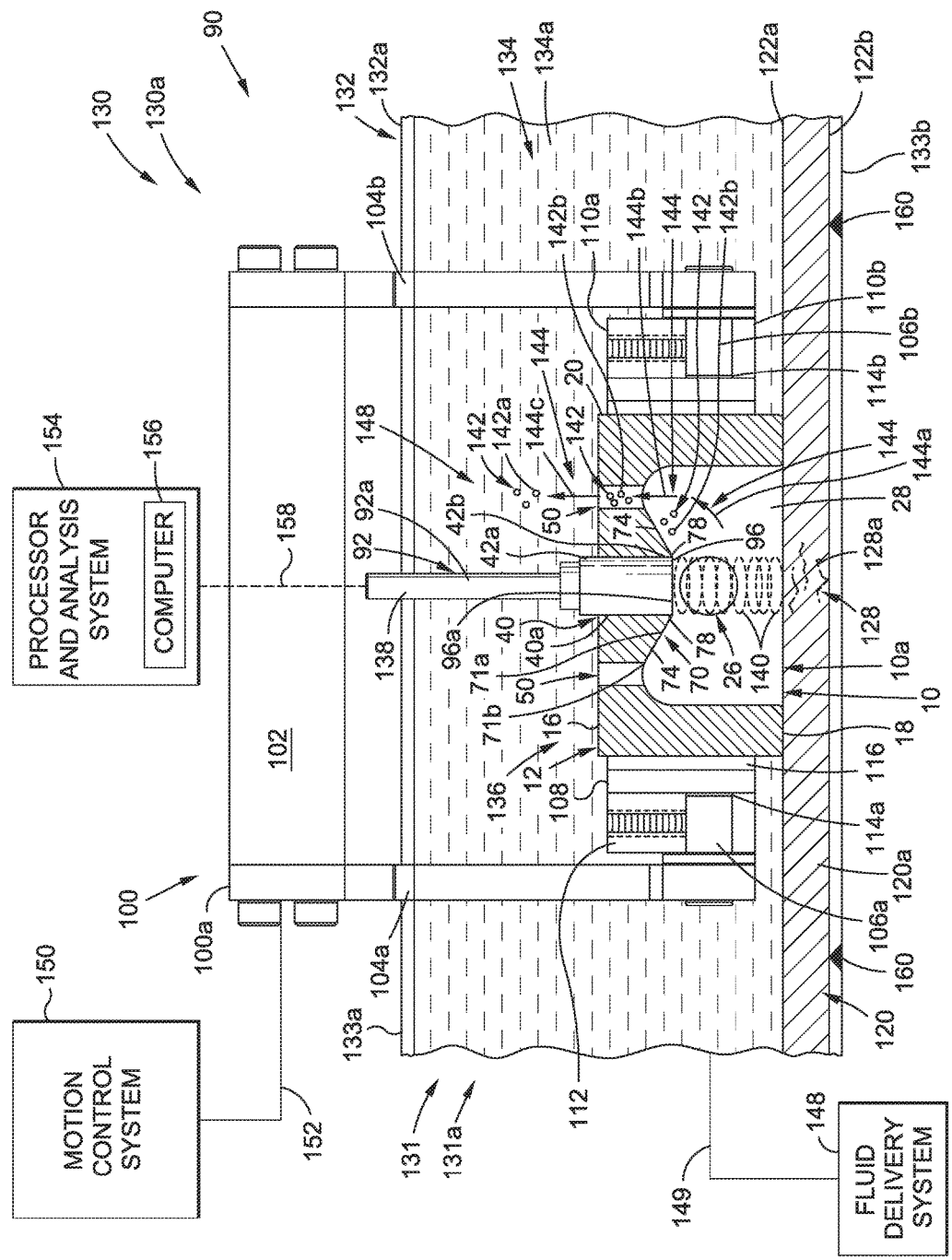

APPARATUS, SYSTEM, AND METHOD FOR REMOVING GAS IN AN IMMERSION ULTRASONIC PROCESS

BACKGROUND

1) Field of the Disclosure

The disclosure relates generally to an apparatus, system, and method for a non-destructive inspection or testing process, and more particularly, to an apparatus, system, and method for removing gas in an immersion ultrasonic non-destructive inspection or testing process performed on a structure, such as an aircraft structure.

2) Description of Related Art

Non-destructive inspection or testing involves examination of a structure without harming the structure or requiring removal or significant disassembly of the structure. Such non-destructive inspection or testing is often used in the aerospace industry to inspect or test aircraft structures, as a quality and process control measure, or for in-service monitoring, and may be performed during manufacturing or after the finished structure has been put into service.

One type of non-destructive inspection or testing includes an immersion ultrasonic process. In an immersion ultrasonic process, an immersion ultrasonic transducer holder is positioned over a structure to be inspected or tested, and an immersion ultrasonic transducer is positioned in the holder. The immersion ultrasonic transducer is positioned to scan the structure without directly contacting the structure. The immersion ultrasonic transducer, the holder, and the structure are immersed in a vessel, such as a tank, filled with a fluid couplant, such as water. Water is a good sound energy couplant between the immersion ultrasonic transducer and the structure to be inspected or tested. Immersion ultrasonic transducers may be used inside a water tank, or as part of a water jet system or a bubbler system, in scanning applications.

The immersion ultrasonic transducer transmits ultrasonic waves, i.e., high frequency sound waves, through the fluid couplant, such as water, and into the structure being inspected or tested. Ultrasonic waves reflected back from the structure to the immersion ultrasonic transducer may be converted into sound pulses or signals of electrical energy that may be processed, displayed, and analyzed to detect any internal irregularities, voids, porosity, disbonds, cracks, or other surface or subsurface structural discontinuities in the structure. Scanning structures with irregular or complex geometries is possible because of the conforming "water path" layer between the immersion ultrasonic transducer and the structure being inspected or tested.

In certain known immersion ultrasonic apparatuses, systems, and processes, during operation, a gas, such as in the form of air bubbles, may form in a flow path or flow chamber of the fluid couplant, such as water. The presence of such air bubbles on or near the face of the immersion ultrasonic transducer may cause an undesirable signal-to-noise ratio, which may decrease the resolution of the scans of the reflected interfaces of the structure being inspected or tested. Such decreased scan resolution may, in turn, lead to inaccurate or misleading inspection results or test data. Due to the need to collect the inspection results or test data from the immersion ultrasonic process quickly, any air bubbles may need to be cleared from or near the face of the immersion ultrasonic transducer within a very short period of time, i.e., within a few seconds.

Known systems and methods exist to remove or minimize the presence of a gas, such as in the form of air bubbles, on or near the face of the immersion ultrasonic transducer during an immersion ultrasonic process. For example, one known method to remove the air bubbles involves manually reorienting the immersion ultrasonic transducer holder, by turning the immersion holder upside down after immersion in the fluid couplant in the vessel, observing any air bubbles, and manually tapping or shaking the holder to force the air bubbles out of the holder and away from the immersion ultrasonic transducer. However, certain immersion ultrasonic transducer holders, such as mounting gimbals, may be difficult to reorient or turn upside down underwater, due to their size and shape, and it may take additional time to move and manually reorient such holders. Moreover, such manual removal of the air bubbles may prove to be an inconsistent solution, if some of the air bubbles are inadvertently missed because they cannot be seen, and are thus not removed.

Another known system and method for removing or minimizing the presence of a gas, such as in the form of air bubbles, on or near the face of the immersion ultrasonic transducer during immersion ultrasonic process involves connecting additional equipment, such as a known vacuum apparatus or system, to the immersion ultrasonic transducer holder to vacuum out or remove the air bubbles on or near the face of the immersion ultrasonic transducer. However, the use of such additional equipment may increase the complexity, setup time, and cost of such known system and method to remove or minimize the presence of such air bubbles.

Accordingly, there is a need in the art for an improved apparatus, system, and method for removing a gas, such as in the form of air bubbles, in an immersion ultrasonic non-destructive inspection or testing process performed on a structure, such as an aircraft structure, that are simple to use, low cost, time efficient, and reliable, and that provide advantages over known apparatuses, systems, and methods.

SUMMARY

Example implementations of this disclosure provide for an improved apparatus, system, and method for removing a gas, such as in the form of air bubbles, in an immersion ultrasonic non-destructive inspection or testing process performed on a structure, such as an aircraft structure. As discussed in the below detailed description, embodiments of the improved apparatus, system, and method may provide significant advantages over known apparatuses, systems, and methods.

In one embodiment there is provided an apparatus for removing a gas in an immersion ultrasonic process. The apparatus comprises an immersion ultrasonic transducer holder apparatus comprising a body with a first end, a second end, a plurality of sides, and a hollow interior cavity portion. The apparatus further comprises a holder portion formed through the first end, and configured to hold one or more immersion ultrasonic transducers in the immersion ultrasonic transducer holder apparatus. The holder portion has an exterior end and an interior end.

The apparatus further comprises a sloped inner face having a base end with a knife-edged perimeter adjacent the interior end of the holder portion. The sloped inner face further has an upward sloped surface extending from the base end to an evacuation end. The apparatus further comprises one or more evacuation ports formed through the first end and located adjacent the evacuation end of the sloped inner face. When the apparatus is used in the immersion ultrasonic process, the knife-edged perimeter, the sloped inner face, and the one or more evacuation ports provide one or more flow paths configured to flow the gas away from the one or more immersion ultrasonic transducers, along the sloped inner face, through the one or more evacuation ports, and out of the apparatus, thus facilitating flow and removal of the gas.

In another embodiment there is provided a system for removing a gas in an immersion ultrasonic process. The system comprises an immersion ultrasonic transducer system comprising an immersion ultrasonic transducer holder apparatus.

The immersion ultrasonic transducer holder apparatus comprises a body with a first end, a second end, a plurality of sides, and a hollow interior cavity portion. The immersion ultrasonic transducer holder apparatus further comprises a holder portion formed through the first end, and having an exterior end and an interior end. The immersion ultrasonic transducer holder apparatus further comprises a sloped inner face having a base end with a knife-edged perimeter adjacent the interior end of the holder portion. The sloped inner face further has an upward sloped surface extending from the base end to an evacuation end. The immersion ultrasonic transducer holder apparatus further comprises one or more evacuation ports formed through the first end and located adjacent the evacuation end of the sloped inner face.

The system further comprises one or more immersion ultrasonic transducers positioned in the immersion ultrasonic transducer holder apparatus. The system further comprises a vessel filled with a fluid couplant. The vessel is configured to hold in the vessel the immersion ultrasonic transducer holder apparatus with the one or more immersion ultrasonic transducers.

The system further comprises an apparatus retaining assembly configured to retain in the vessel the immersion ultrasonic transducer holder apparatus with the one or more immersion ultrasonic transducers, when the one or more immersion ultrasonic transducers scan a structure during the immersion ultrasonic process.

During the immersion ultrasonic process, the immersion ultrasonic transducer holder apparatus and the one or more immersion ultrasonic transducers held in the immersion ultrasonic transducer holder apparatus are immersed in the vessel filled with the fluid couplant. The knife-edged perimeter, the sloped inner face, and the one or more evacuation ports provide one or more flow paths configured to flow the gas comprising one or more air bubbles, away from the one or more immersion ultrasonic transducers, along the sloped inner face, through the one or more evacuation ports, and out of the immersion ultrasonic transducer holder apparatus, thus facilitating flow and removal of the gas.

In another embodiment there is provided a method for removing a gas in an immersion ultrasonic process. The method comprises the step of using an immersion ultrasonic transducer holder apparatus.

The immersion ultrasonic transducer holder apparatus comprises a body with a first end, a second end, a plurality of sides, and a hollow interior cavity portion. The apparatus further comprises a holder portion formed through the first end, and having an exterior end and an interior end. The apparatus further comprises a sloped inner face having a base end with a knife-edged perimeter adjacent the interior end of the holder portion. The sloped inner face further has an upward sloped surface extending from the base end to an evacuation end. The apparatus further comprises one or more evacuation ports formed through the first end and located adjacent the evacuation end of the sloped inner face.

The method further comprises the step of positioning one or more immersion ultrasonic transducers in the immersion ultrasonic transducer holder apparatus. The method further comprises the step of retaining the immersion ultrasonic transducer holder apparatus with the one or more immersion ultrasonic transducers, in an apparatus retaining assembly, to obtain an immersion ultrasonic transducer assembly.

The method further comprises the step of immersing the immersion ultrasonic transducer assembly into a vessel filled with a fluid couplant and a structure configured to undergo the immersion ultrasonic process. The method further comprises using the knife-edged perimeter, the sloped inner face, and the one or more evacuation ports, during the immersion ultrasonic process, to flow and remove the gas comprising one or more air bubbles, away from the one or more immersion ultrasonic transducers, along the sloped inner face, through the one or more evacuation ports, and out of the immersion ultrasonic transducer holder apparatus.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate exemplary embodiments, but which are not necessarily drawn to scale, wherein:

FIG. 3A is a schematic diagram of an exemplary embodiment of a system of the disclosure;

Figure 1A:
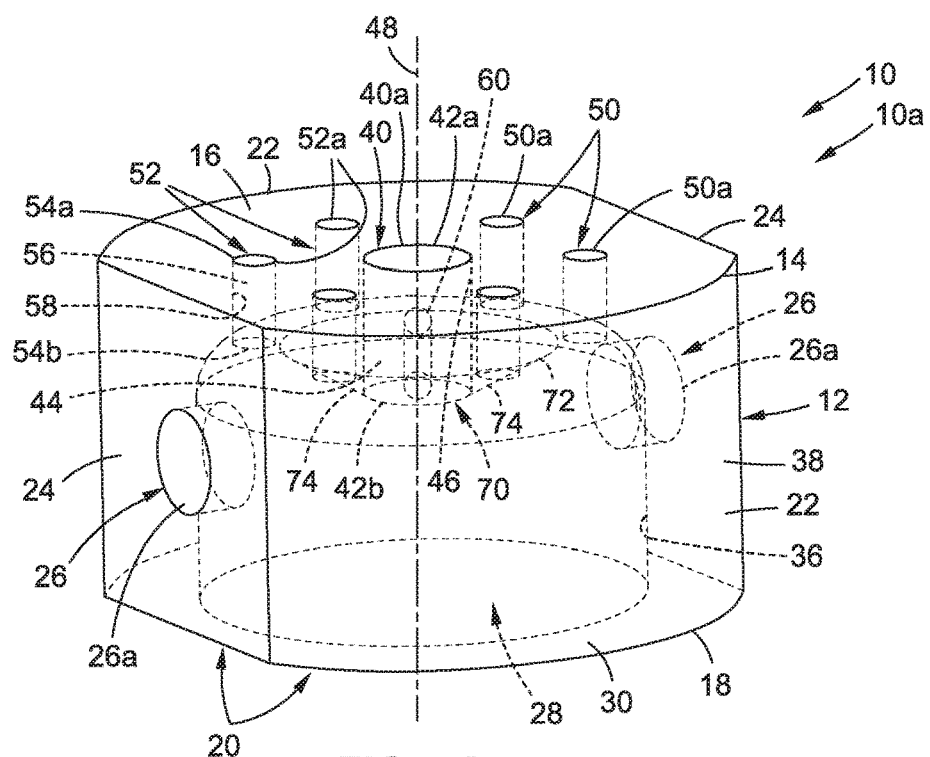
FIG. 1A is an illustration of a front side perspective view of an exemplary embodiment of an apparatus of the disclosure, in the form of an immersion ultrasonic transducer holder apparatus.

Each figure shown in this disclosure shows a variation of an aspect of the embodiments presented, and only differences will be discussed in detail.

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and fully convey the scope of the disclosure to those skilled in the art.

Now referring to the Figures, FIGS. 1A-1G show various views of an exemplary embodiment of an apparatus 10, such as in the form of an immersion ultrasonic transducer holder apparatus 10a. In one embodiment, there is provided the apparatus 10, such as in the form of an immersion ultrasonic transducer holder apparatus 10a, for removing a gas 142 (see FIG. 3A) in an immersion ultrasonic process 131 (see FIG. 3A). The gas 142 (see FIG. 3A) may comprise air 142a (see FIG. 3A) or another type of gas. The air 142a (see FIG. 3A) is in the form of air bubbles 142b (see FIG. 3A), or another form of air.

Figure 1B:
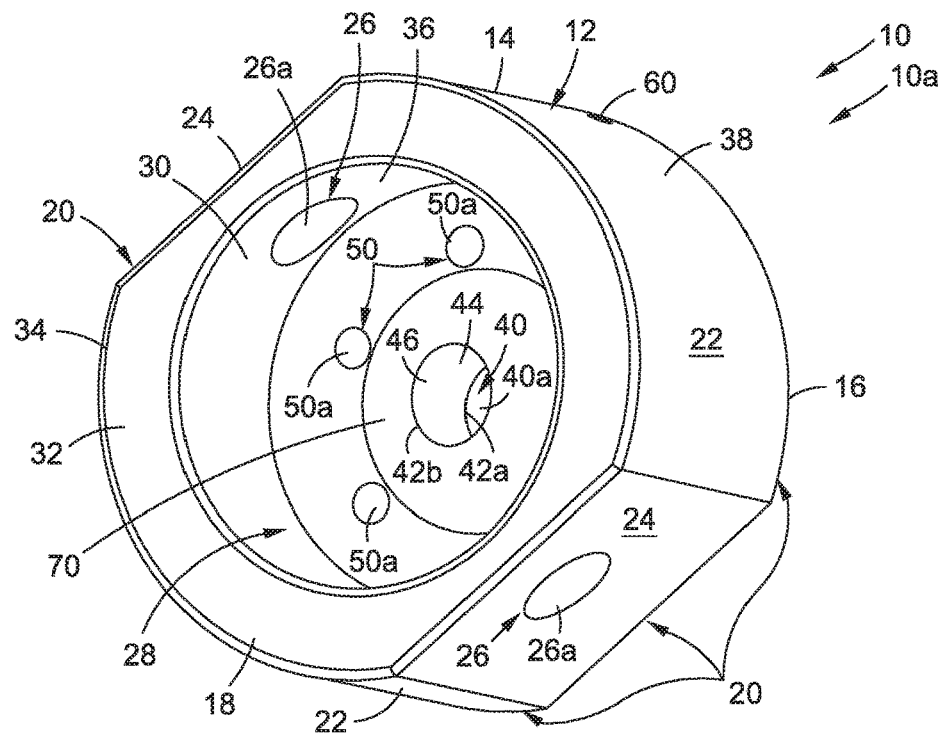
FIG. 1B an illustration of a bottom perspective view of the apparatus of FIG. 1A.
Figure 1C:
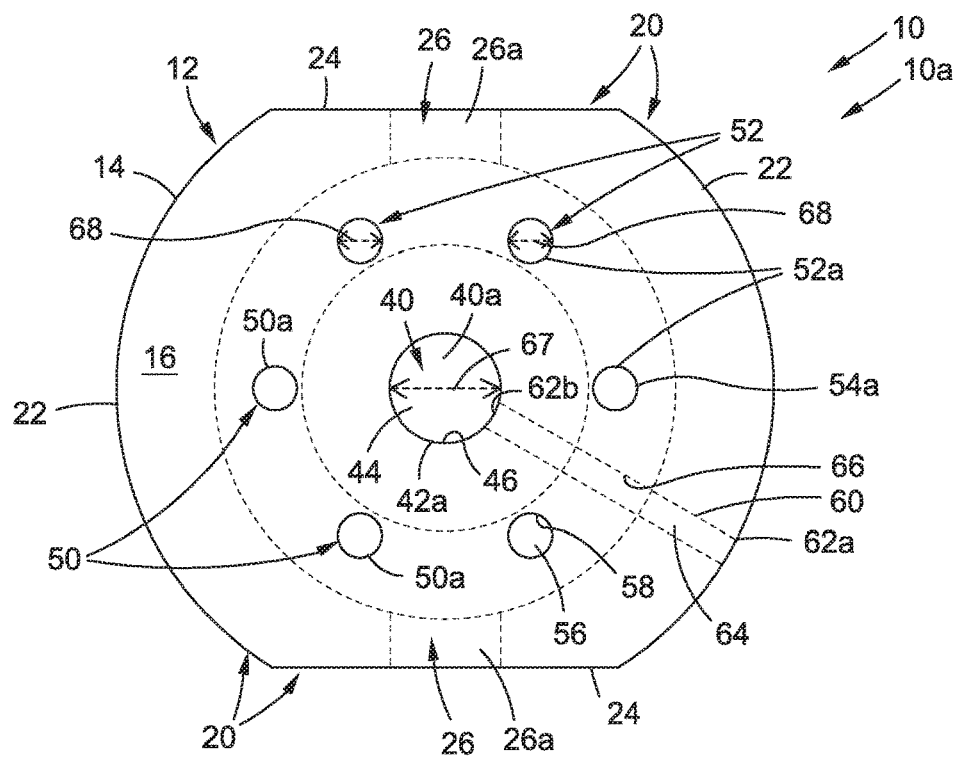
FIG. 1C an illustration of a top view of the apparatus of FIG. 1A.
Figure 1D:
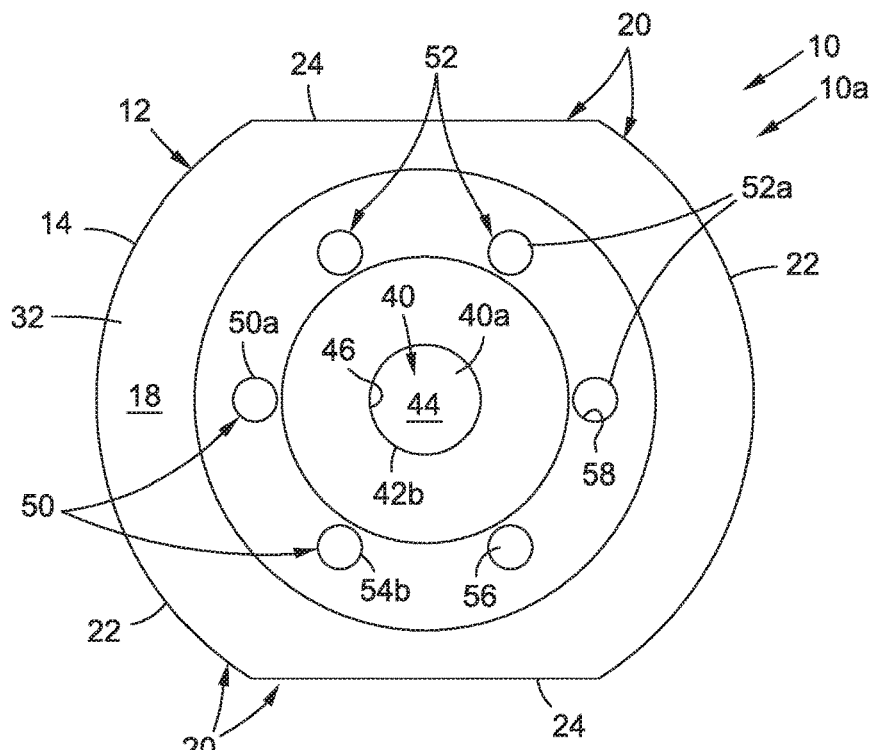
FIG. 1D an illustration of a bottom view of the apparatus of FIG. 1A.
Figure 1E:
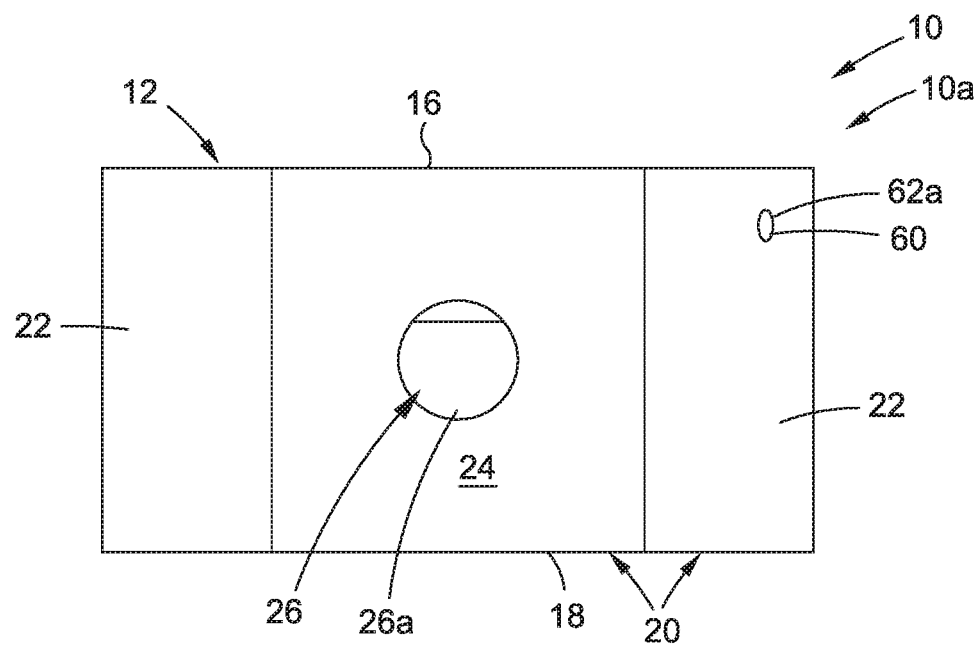
FIG. 1E an illustration of a front view of the apparatus of FIG. 1A.
Figure 1F:
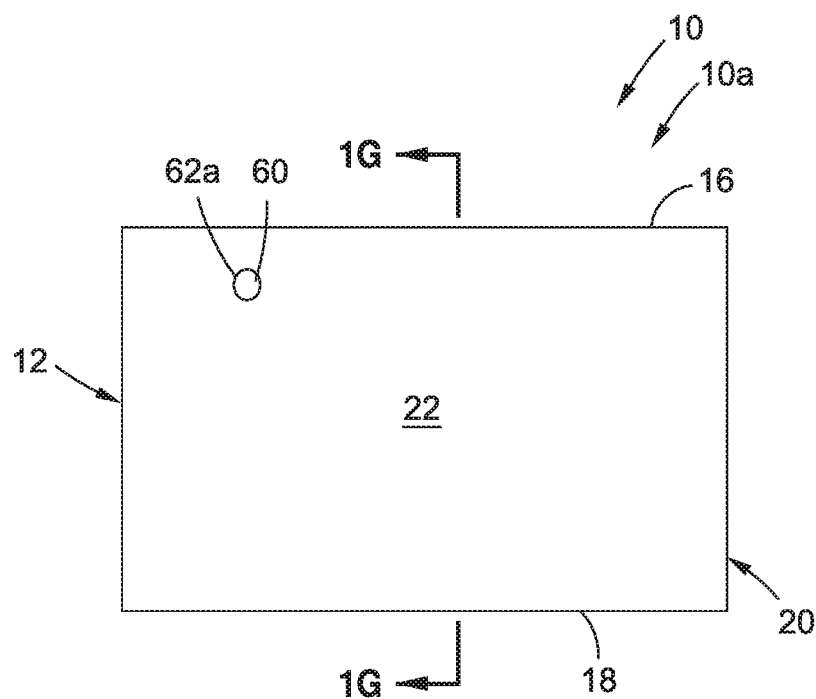
FIG. 1F an illustration of a right side view of the apparatus of FIG. 1A.
Figure 1G:
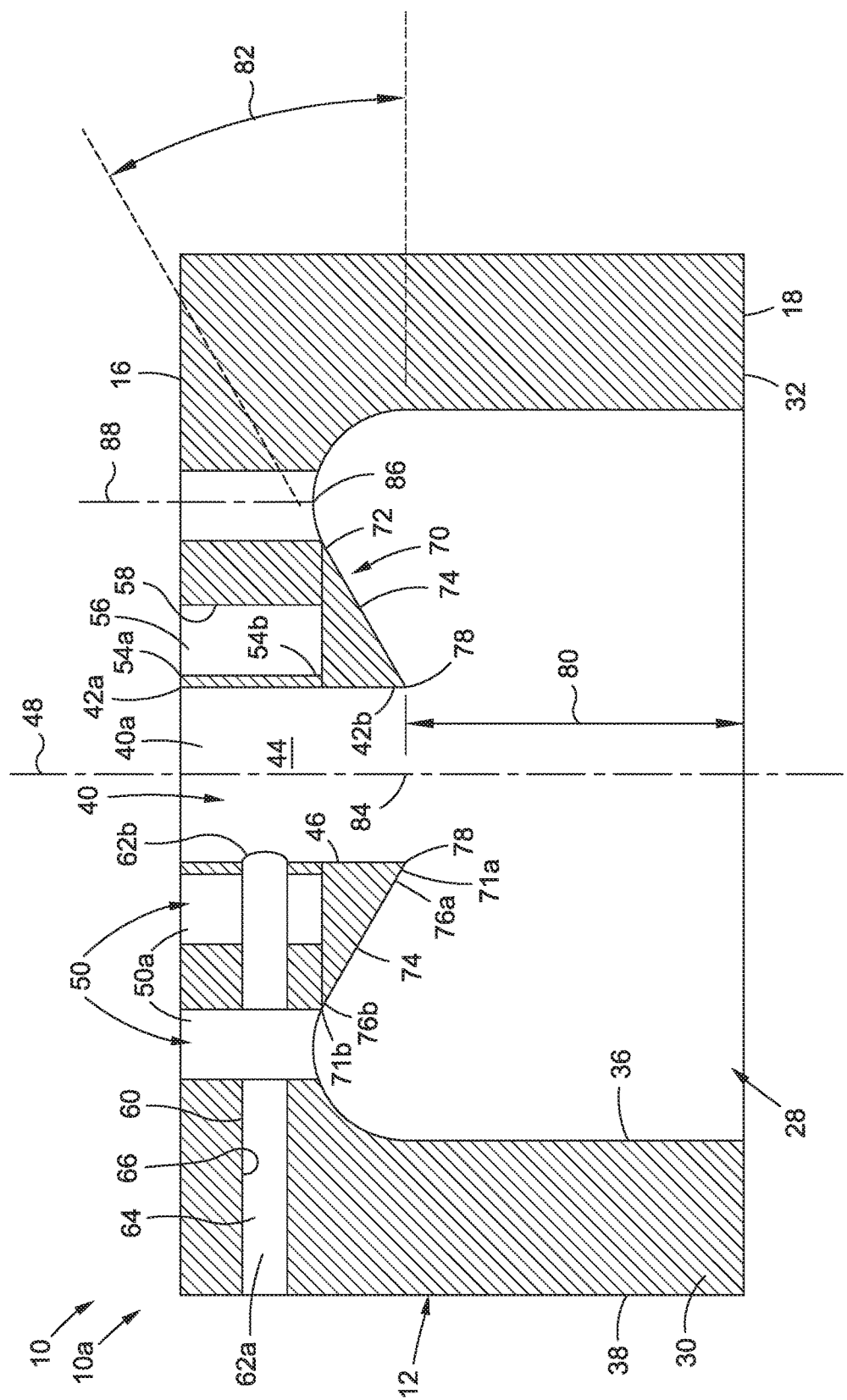
FIG. 1G an illustration of a cross-sectional view of the apparatus of FIG. 1A, taken along lines 1G-1G of FIG. 1F.

FIG. 1A is an illustration of a front side perspective view of an exemplary embodiment of the apparatus 10, such as in the form of the immersion ultrasonic transducer holder apparatus 10a, of the disclosure. FIG. 1B an illustration of a bottom perspective view of the apparatus 10, such as in the form of the immersion ultrasonic transducer holder apparatus 10a, of FIG. 1A. FIG. 1C an illustration of a top view of the apparatus 10, such as in the form of the immersion ultrasonic transducer holder apparatus 10a, of FIG. 1A. FIG. 1D an illustration of a bottom view of the apparatus 10, such as in the form of the immersion ultrasonic transducer holder apparatus 10a, of FIG. 1A. FIG. 1E an illustration of a front view of the apparatus 10, such as in the form of the immersion ultrasonic transducer holder apparatus 10a, of FIG. 1A. FIG. 1F an illustration of a right side view of the apparatus 10, such as in the form of the immersion ultrasonic transducer holder apparatus 10a, of FIG. 1A. FIG. 1G an illustration of a cross-sectional view of the apparatus 10, such as in the form of the immersion ultrasonic transducer holder apparatus 10a, of FIG. 1A, taken along lines 1G-1G of FIG. 1F.

The apparatus 10 (see FIGS. 1A-1G), such as in the form of the immersion ultrasonic transducer holder apparatus 10a (see FIGS. 1A-1G), may also be referred to as an immersion ultrasonic transducer shoe. The apparatus 10 (see FIGS. 1A-1G), such as in the form of the immersion ultrasonic transducer holder apparatus 10a (see FIGS. 1A-1G), comprises a body 12 (see FIGS. 1A-1G). As shown in FIGS. 1A-1D, the body 12 may have a substantially cylindrical configuration 14. However, the body 12 (see FIGS. 1A-1D) may also have another suitable shape or configuration.

The body 12 (see FIGS. 1A-1G) has a first end 16 (see FIGS. 1A, 1C, 1E-1G) and a second end 18 (see FIGS. 1A-1B, 1D-1G). The body 12 (see FIGS. 1A-1D) further has a plurality of sides 20 (see FIGS. 1A-1D) disposed between the first end 16 (see FIGS. 1A, 1C) and the second end 18 (see FIGS. 1A-1B). The plurality of sides 20 (see FIGS. 1A-1F) may comprise curved sides 22 (see FIGS. 1A-1F) and flat sides 24 (see FIGS. 1A-1E) or other suitably shaped sides. As shown in FIGS. 1A-1D, the plurality of sides 20 comprise alternating curved sides 22 and flat sides 24, with two curved sides 22 of substantially the same size and shape positioned opposite each other, and two flat sides 24 of substantially the same size and shape positioned opposite each other. However, the plurality of sides 20 (see FIG. 1A) may comprise all flat sides 24, no flat sides 24, any number of a combination of flat sides 24 and curved sides 22, or other suitably shaped sides.

The plurality of sides 20 (see FIGS. 1A-1B, 1E) may include two or more attachment points 26 (see FIGS. 1A-1B, 1E), such as in the form of through opening attachment points 26a (see FIGS. 1A-1B, 1E), formed through two or more of the plurality of sides 20. As shown in FIGS. 1A-1B, the attachment points 26, such as in the form of through opening attachment points 26a, are formed through the flat sides 24 of the body 12. However, the attachment points 26 may be formed through, or in, the curved sides 22 (see FIG. 1A), or through, or in, other suitably shaped sides of the body 12. The two or more attachment points 26 (see FIGS. 1A-1B) are configured for attachment to an apparatus retaining assembly 100 (see FIGS. 2A-2B), such as in the form of a gimbal assembly 100a (see FIGS. 2A-2B) (discussed in further detail below), when the apparatus 10 (see FIG. 3A) is used in the immersion ultrasonic process 131 (see FIG. 3A).

The body 12 (see FIGS. 1A-1G) further comprises a hollow interior cavity portion 28 (see FIGS. 1A-1B, 1G) surrounded by a solid interior portion 30 (see FIGS. 1A-1B, 1G). As shown in FIGS. 1B, 1G, the solid interior portion 30 of the body 12 has a guide surface 32 for guiding or moving the apparatus 10 along a structure 120 (see FIG. 3A), during the immersion ultrasonic process 131 (see FIG. 3A). As shown in FIG. 1B, the guide surface 32 has a rim portion 34 surrounding or framing the guide surface 32.

As shown in FIGS. 1A-1B and 1G, the apparatus 10, such as in the form of the immersion ultrasonic transducer holder apparatus 10a, has an interior surface 36 and an exterior surface 38. As shown in FIG. 1B, the interior surface 36, such as in the form of a curved wall, is substantially cylindrical in shape. However, the interior surface 36 may be of another suitable shape or configuration.

As shown in FIGS. 1A-1D and 1G, the apparatus 10, such as in the form of the immersion ultrasonic transducer holder apparatus 10a, further comprises a holder portion 40, such as in the form of a through opening holder portion 40a, formed through the first end 16 of the body 12. The holder portion 40 (see FIGS. 1A-1D, 1G), such as in the form of the through opening holder portion 40a (see FIGS. 1A-1D, 1G), has an exterior end 42a (see FIGS. 1A-1C, 1G), an interior end 42b (see FIGS. 1A-1B, 1D, 1G), a hollow interior 44 (see FIGS. 1A-1D, 1G), and a holder portion interior wall 46 (see FIGS. 1A-1D, 1G). As shown in FIGS. 1A-1B, the holder portion interior wall 46, such as in the form of a curved wall, is substantially cylindrical in shape. However, the holder portion interior wall 46 may be of another suitable shape or configuration. As shown in FIG. 1C, the holder portion 40 has a diameter 67, and the diameter 67 of the holder portion 40 is preferably greater than a diameter 68 of an evacuation port 50, discussed below.

As shown in FIGS. 1A and 1G, the holder portion 40, such as in the form of the through opening holder portion 40a, is preferably centrally located in and through the first end 16 of the body 12 of the apparatus 10, and the holder portion interior wall 46 is preferably parallel to a central axis 48 running through the center of the holder portion 40. Alternatively, the holder portion 40 may be located in and through another location of the first end 16 of the body 12 of the apparatus 10.

The holder portion 40 (see FIGS. 1A, 3A), such as the through opening holder portion 40a (see FIGS. 1A, 3A), is configured to hold one or more immersion ultrasonic transducers 92 (see FIG. 3A) in the apparatus 10 (see FIG. 3A), such as the immersion ultrasonic transducer holder apparatus 10a (see FIG. 3A). The immersion ultrasonic transducer 92 (see FIG. 2B) is discussed in detail below with regard to FIG. 2B.

As shown in FIGS. 1A-1D and 1G, the apparatus 10, such as in the form of the immersion ultrasonic transducer holder apparatus 10a, further comprises one or more evacuation ports 50, such as in the form of through opening evacuation ports 50a, formed through the first end 16 of the body 12. As shown in FIGS. 1A-1D, the apparatus 10, such as in the form of the immersion ultrasonic transducer holder apparatus 10a, comprises six (6) evacuation ports 50 surrounding the holder portion 40. However, the number of evacuation ports 50 surrounding the holder portion 40 may be less than six (6), or more than six (6), depending on the size and shape of the apparatus 10. The one or more evacuation ports 50 (see FIGS. 1A-1D, 1G) are preferably each vertically oriented and may be positioned or formed in a pattern 52 (see FIGS. 1A, 1C-1D), such as a uniform radial pattern 52a (see FIGS. 1A, 1C-1D), or another suitable pattern, around or near the holder portion 40 (see FIGS. 1A, 1C-1D).

The one or more evacuation ports 50 (see FIGS. 1A, 1G), such as in the form of through opening evacuation ports 50a (see FIGS. 1A, 1G), each comprises an exterior end 54a (see FIGS. 1A, 1C, 1G), an interior end 54b (see FIGS. 1A, 1D, 1G), a hollow interior 56 (see FIGS. 1A, 1C-1D, 1G), and an evacuation port interior wall 58 (see FIGS. 1A, 1C-1D, 1G). The evacuation port interior wall 58 (see FIGS. 1A, 1C-1D, 1G) of each evacuation port 50 (see FIGS. 1A, 1C-1D, 1G) is preferably parallel to the holder portion interior wall 46 (see FIGS. 1A-1D, 1G) of the holder portion 40 (see FIGS. 1A-1D, 1G). As shown in FIG. 1C, each evacuation port 50 has a diameter 68, and the diameter 68 of the evacuation port 50 is less than the diameter 67 of the holder portion 40.

As shown in FIGS. 1A-1C and 1E-1G, the apparatus 10, such as in the form of the immersion ultrasonic transducer holder apparatus 10a, may further comprise one or more fluid evacuation channels 60. Each fluid evacuation channel 60 (see FIGS. 1C, 1G) has an exterior end 62a (see FIGS. 1C, 1G), an interior end 62b (see FIGS. 1C, 1G), a hollow interior 64 (see FIGS. 1C, 1G), and a channel interior wall 66 (see FIGS. 1C, 1G). Each fluid evacuation channel 60 (see FIGS. 1C, 1G) preferably is formed through the body 12 and extends continuously from the interior end 62b which intersects the holder portion 40, to the exterior end 62a which intersects an exterior surface 38 of the apparatus 10.

As shown in FIGS. 1A-1D and 1G, the apparatus 10, such as in the form of the immersion ultrasonic transducer holder apparatus 10a, further comprises a sloped inner face 70. The sloped inner face 70 (see FIG. 1G) has a base end 71a (see FIG. 1G) with a knife-edged perimeter 78 (see FIG. 1G) adjacent the interior end 42b (see FIG. 1G) of the holder portion 40 (see FIG. 1G). As shown in FIGS. 1A and 1G, the sloped inner face 70 has a conical-shaped configuration 72, and an upward sloped surface 74 with a first end 76a (see FIG. 1G), such as in the form of base end 71a, and a second end 76b (see FIG. 1G), such as in the form of evacuation end 71b. The upward sloped surface 74 (see FIG. 1G) is preferably sloped at an angle 82 (see FIG. 1G) of from about 20° (twenty degrees) to about 70° (seventy degrees). More preferably, the upward sloped surface 74 (see FIG. 1G) is preferably sloped at an angle 82 (see FIG. 1G) from the transducer face 96 (see FIG. 3A) of about 30° (thirty degrees). As shown in FIG. 1G, the one or more evacuation ports 50 are located adjacent the evacuation end 71b of the sloped inner face 70.

As further shown in FIG. 1G, the immersion ultrasonic transducer holder apparatus 10a provides a consistent offset distance 80 between the interior end 42b of the holder portion 40 configured to hold the immersion ultrasonic transducer 92 (see FIG. 2B), and a structure 120 (see FIG. 3A), during the immersion ultrasonic process 131 (see FIG. 3A). As further shown in FIG. 1G, a first tangency point 84 through the central axis 48 of the holder portion 40 is shown, and a second tangency point 86 through a central axis 88 of the evacuation port 50 is shown. The upward sloped surface 74 (see FIG. 1G) is preferably sloped at an angle 82 (see FIG. 1G) formed by a line from the first tangency point 84 to the second tangency point 86 and a line perpendicular to the central axis 48 of the holder portion 40.

When the apparatus 10 (see FIGS. 1A-1G), such as in the form of the immersion ultrasonic transducer holder apparatus 10a (see FIGS. 1A-1G), is used in the immersion ultrasonic process 131 (see FIG. 3A), the apparatus 10 (see FIGS. 1A-1G) comprising the immersion ultrasonic transducer holder apparatus 10a (see FIGS. 1A-1G), and the immersion ultrasonic transducer 92 (see FIGS. 2B, 3A) held in the immersion ultrasonic transducer holder apparatus 10a (see FIGS. 1A-1G), are immersed in a vessel 132 (see FIG. 3A) filled with a fluid couplant 134 (see FIG. 3A), such as water 134a (see FIG. 3A). The knife-edged perimeter 78 (see FIGS. 1G, 3A), the sloped inner face 70 (see FIGS. 1A, 1G, 3A), and the one or more evacuation ports 50 (see FIGS. 1A, 1G, 3A) provide one or more flow paths 144 (see FIG. 3A) configured to flow the gas 142 (see FIG. 3A), such as air bubbles 142b (see FIG. 3A), that may be trapped at the immersion ultrasonic transducer 92 (see FIG. 3A) or transducer face 96 (see FIG. 3A), away from the immersion ultrasonic transducer 92 (see FIG. 3A) or transducer face 96 (see FIG. 3A), and along the sloped inner face 70 (see FIG. 3A), through the one or more evacuation ports 50 (see FIG. 3A), and out of the apparatus 10 (see FIG. 3A), such as in the form of the immersion ultrasonic transducer holder apparatus 10a (see FIG. 3A), thus facilitating flow and removal of the gas 142 (see FIG. 3A).

Figure 2A:
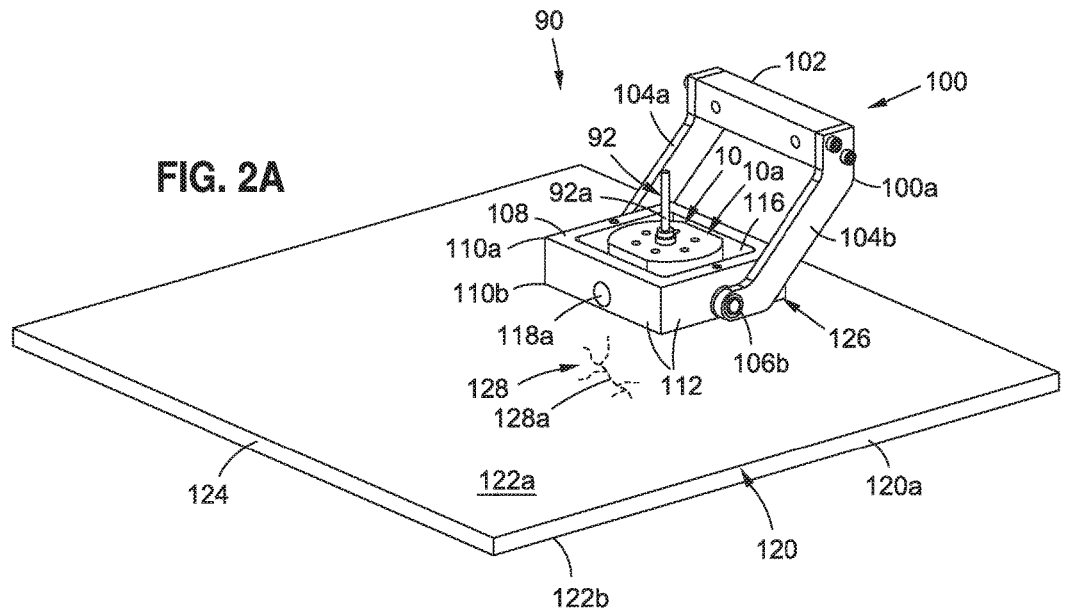
FIG. 2A is an illustration of a perspective view of an exemplary embodiment of an immersion ultrasonic transducer assembly of the disclosure.
Figure 2B:
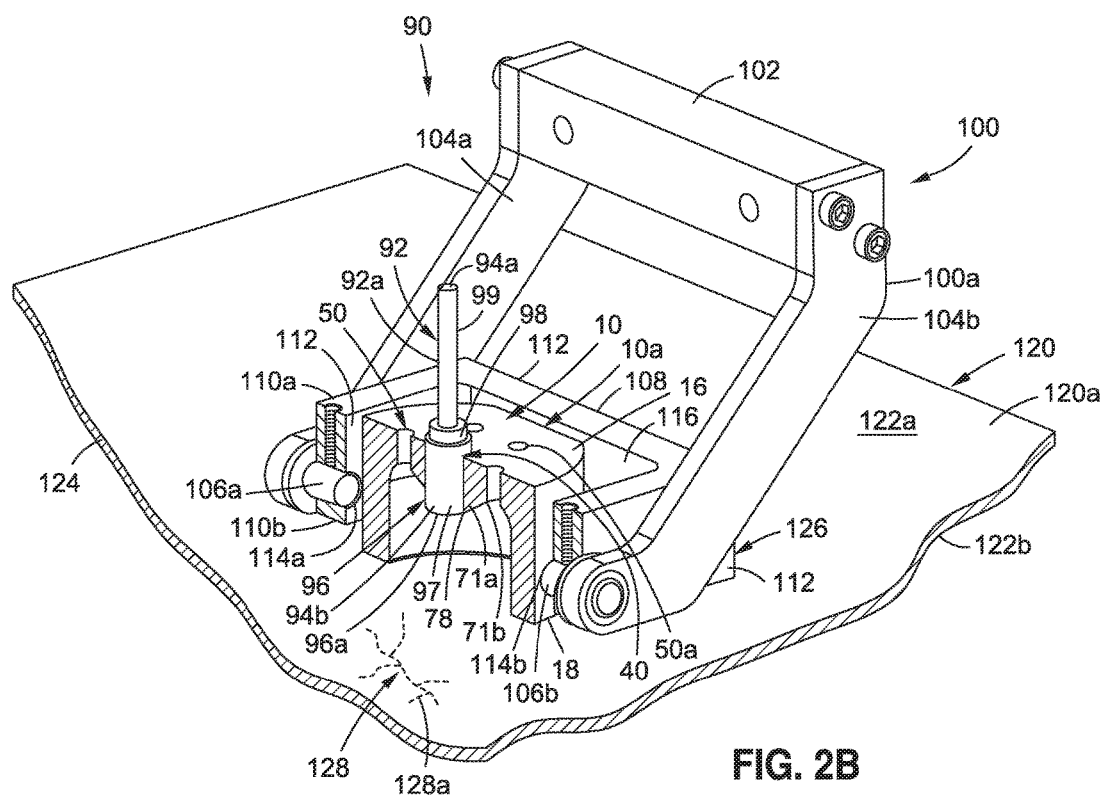
FIG. 2B is an illustration of a partial cutaway perspective view of the immersion ultrasonic transducer assembly of FIG. 2A.
Figure 2C:
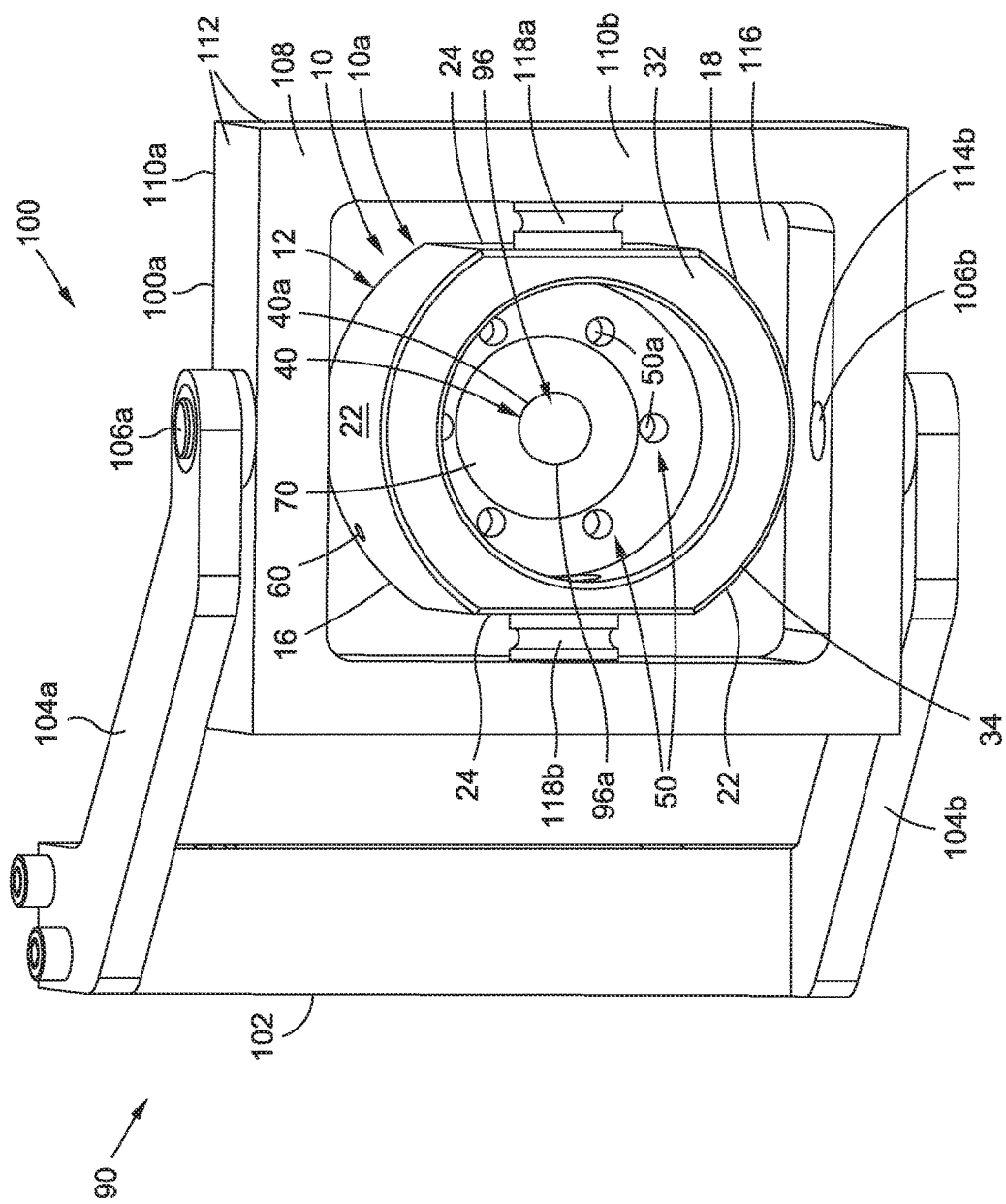
FIG. 2C is an illustration of a bottom perspective view of an embodiment of the immersion ultrasonic transducer holder apparatus installed in an apparatus retaining assembly of the immersion ultrasonic transducer assembly of FIG. 2A.

Referring now to FIGS. 2A-2C, FIG. 2A is an illustration of a perspective view of an exemplary embodiment of an immersion ultrasonic transducer assembly 90 of the disclosure. FIG. 2B is an illustration of a partial cutaway perspective view of the immersion ultrasonic transducer assembly 90 of FIG. 2A. FIG. 2C is an illustration of a bottom perspective view of an embodiment of the immersion ultrasonic transducer holder apparatus 10a installed in an apparatus retaining assembly 100 of the immersion ultrasonic transducer assembly 90 of FIG. 2A.

As shown in FIGS. 2A-2B, the immersion ultrasonic transducer assembly 90 comprises the apparatus 10, such as in the form of immersion ultrasonic transducer holder apparatus 10a, comprises the immersion ultrasonic transducer 92, such as in the form of an immersion ultrasonic sensor probe 92a, inserted in the holder portion 40 (see FIG. 2B) of the apparatus 10, and comprises an apparatus retaining assembly 100 for retaining or securing the apparatus 10 and the immersion ultrasonic transducer 92.

As further shown in FIGS. 2A-2B, the immersion ultrasonic transducer assembly 90 is positioned in an operating position 126 and is configured to move across a structure 120, such as a part 120a, in order to scan the structure 120 with the immersion ultrasonic transducer 92. The structure 120 (see FIGS. 2A-2B), such as the part 120a (see FIGS. 2A-2B), has a first surface 122a (see FIGS. 2A-2B), a second surface 122b (see FIGS. 2A-2B), and a body 124 (see FIGS. 2A-2B) therebetween. The part 120a (see FIGS. 2A-2B) may comprise a test specimen part, a manufactured part, or another suitable part, and may be made of a composite material, a metal material, or a mixture of a composite material and a metal material. The structure 120 (see FIGS. 2A-2B) may undergo the immersion ultrasonic process 131 (see FIG. 3A) for inspection or testing, to identify any subsurface or surface irregularities, cracks, voids, porosity, disbonds, structural discontinuities, material characteristics, material changes, or other subsurface or surface features in the structure. As shown in FIGS. 2A-2B, the structure 120, such as in the form of part 120a, has a subsurface irregularity 128, such as in the form of a subsurface crack 128a.

As shown in FIG. 2B, the immersion ultrasonic transducer 92, such as in the form of an immersion ultrasonic sensor probe 92a, comprises a first end 94a, a second end 94b, a transducer face 96 having a circumference 96a, a casing portion 97, a connector portion 98, and a probe portion 99. The casing portion 97 (see FIG. 2B) and the connector portion 98 (see FIG. 2B) of the immersion ultrasonic transducer 92 (see FIG. 2B) may be made of a metal material or another suitably hard and durable material. The transducer face 96 (see FIG. 2B) and the probe portion 99 (see FIG. 2B) may be made of a hard and durable plastic material or another suitable material.

As shown in FIG. 2B, the knife-edged perimeter 78 surrounds the circumference 96a of the transducer face 96 of the immersion ultrasonic transducer 92. The base end 71a (see FIG. 2B) of the sloped inner face 70 (see FIGS. 1A, 1G) is also adjacent or near the circumference 96a of the transducer face 96. FIG. 2B further shows the evacuation end 71b adjacent or near the evacuation ports 50, such as the through opening evacuation ports 50a, surrounding the holder portion 40.

As shown in FIG. 2C, the bottom view of the apparatus 10, such as in the form of immersion ultrasonic transducer holder apparatus 10a, shows the transducer face 96 with the circumference 96a, of the immersion ultrasonic transducer 92 inserted and retained in the holder portion 40, such as the through opening holder portion 40a. The sloped inner face 70 (see FIG. 2C) extends from the transducer face 96 (see FIG. 2C) in the holder portion 40 (see FIG. 2C), to the evacuation ports 50 (see FIG. 2C), such as in the form of through opening evacuation ports 50a (see FIG. 2C). FIG. 2C further shows the first end 16, the second end 18, the curved sides 22, the flat sides 24, the guide surface 32 with the rim portion 34, and the fluid evacuation channel 60, of the apparatus 10.

The immersion ultrasonic transducer 92 (see FIGS. 2A-2B) is preferably a known immersion ultrasonic transducer designed to operate in a liquid or fluid environment and all connections of the immersion ultrasonic transducer are watertight and sealed. The immersion ultrasonic transducer 92 (see FIGS. 2A-2B) is designed to be immersed in a fluid couplant 134 (see FIG. 3A), such as water 134 (see FIG. 3A), for example, filtered water, to couple sound energy into the structure 120 (see FIGS. 2A-2B), such as the part 120a (see FIGS. 2A-2B). The immersion ultrasonic transducer 92 (see FIGS. 2A-2B) does not contact the structure 120 (see FIGS. 2A-2B, 3A) during the immersion ultrasonic process 131 (see FIG. 3A). The immersion ultrasonic transducer 92 further comprises known internal components within the casing portion 97 or within the probe portion 98, such as one or more of the following, for example, one or more piezoelectric sensors or other types of sensors; a planer, cylindrically focused, or spherically focused acoustic lens for focusing the ultrasound waves or beams to a smaller area; damping material for quieting the transducer; an impedance matching layer that helps to get more sound energy into the water and, in turn, into the structure being inspected or tested; electrical connections and wiring, or other suitable components.

The apparatus 10 (see FIGS. 2A-2B), such as the immersion ultrasonic transducer holder apparatus 10a (see FIGS. 2A-2B), of the immersion ultrasonic transducer assembly 90 (see FIGS. 2A-2B), may comprise one immersion ultrasonic transducer 92 (see FIGS. 2A-2B) in the holder portion 40 (see FIG. 2B). Alternatively, the apparatus 10, such as the immersion ultrasonic transducer holder apparatus 10a, of the immersion ultrasonic transducer assembly 90, may comprise an assembly or array of multiple individual immersion ultrasonic transducers 92 in a single assembly or array. For example, phased array probes may use multiple individual immersion ultrasonic transducers to generate steered ultrasound waves or beams in a single assembly.

The immersion ultrasonic transducer 92 (see FIGS. 2A-2B) may have a frequency in a range of about 0.5 MHz (megahertz) to 20 MHz, or greater, and preferably, may have a frequency in a range of about 1 MHz to 10 MHz. The immersion ultrasonic transducer 92 (see FIGS. 2A-2B) may be of a size having a diameter in a range of about greater than 0 inch to 2 inches, or preferably, ¼ inch to 2 inches, or greater, and is dependent on the size of the immersion ultrasonic transducer holder apparatus 10a (see FIGS. 1A-1G) and the holder portion 40 (see FIGS. 1A-1B). Bandwidth, or the span of frequencies contained in the spectrum generated by the immersion ultrasonic transducer 92 (see FIGS. 2A-2B), may be either narrow or broad.

As shown in FIGS. 2A-2C, the apparatus retaining assembly 100, such as in the form of a gimbal assembly 100a, comprises a handle portion 102 coupled to arm portions 104a, 104b. Arm portion 104a (see FIGS. 2B-2C) has a pivot pin 106a (see FIGS. 2B-2C) configured for insertion into pivot pin hole 114a (see FIG. 2B), and arm portion 104b (see FIGS. 2A-2C) has a pivot pin 106b (see FIGS. 2A-2C) configured for insertion into pivot pin hole 114b (see FIGS. 2B-2C).

As further shown in FIGS. 2A-2C, the apparatus retaining assembly 100, such as in the form of gimbal assembly 100a, comprises an apparatus enclosure portion 108 having a first end 110a, a second end 110b, a plurality of walls 112, and an open interior 116. The pivot pin holes 114a, 114b (see FIGS. 2B-2C) are preferably formed through two of the walls 112 (see FIGS. 2B-2C) opposite each other. However, the pivot pin holes 114a, 114b (see FIGS. 2B-2C) may be formed through more than two walls or through one wall 112. The apparatus enclosure portion 108 (see FIGS. 2A-2C) is preferably of a sufficient size and shape to surround and enclose the apparatus 10 (see FIGS. 2A-2C), such as in the form of immersion ultrasonic transducer holder apparatus 10a (see FIGS. 2A-2C). As shown in FIG. 2B, the first end 16 of the apparatus 10 is enclosed by, and is preferably in the same or substantially the same plane as the first end 110a of the apparatus enclosure portion 108. As further shown in FIG. 2B, the second end 18 of the apparatus 10 is enclosed by, and is preferably in the same plane as the second end 110*b* of the apparatus enclosure portion 108.

The apparatus retaining assembly 100, such as in the form of gimbal assembly 100*a*, further comprises retaining members 118*a*, 118*b* (see FIGS. 2A, 2C) for retaining the apparatus 10 (see FIGS. 2A-2C), such as the immersion ultrasonic transducer holder apparatus 10*a* (see FIGS. 2A-2C), within the open interior 116 (see FIGS. 2A-2C) of the apparatus enclosure portion 108 (see FIGS. 2A-2C). The retaining members 118*a*, 118*b* (see FIG. 2C) are configured for insertion into respective attachment points 26 (see FIG. 1) formed through the flat sides 24 (see FIGS. 1A, 2C) of the body 12 (see FIGS. 1A, 2C) of the apparatus 10 (see FIGS. 1A, 2C).

Figure 3B:
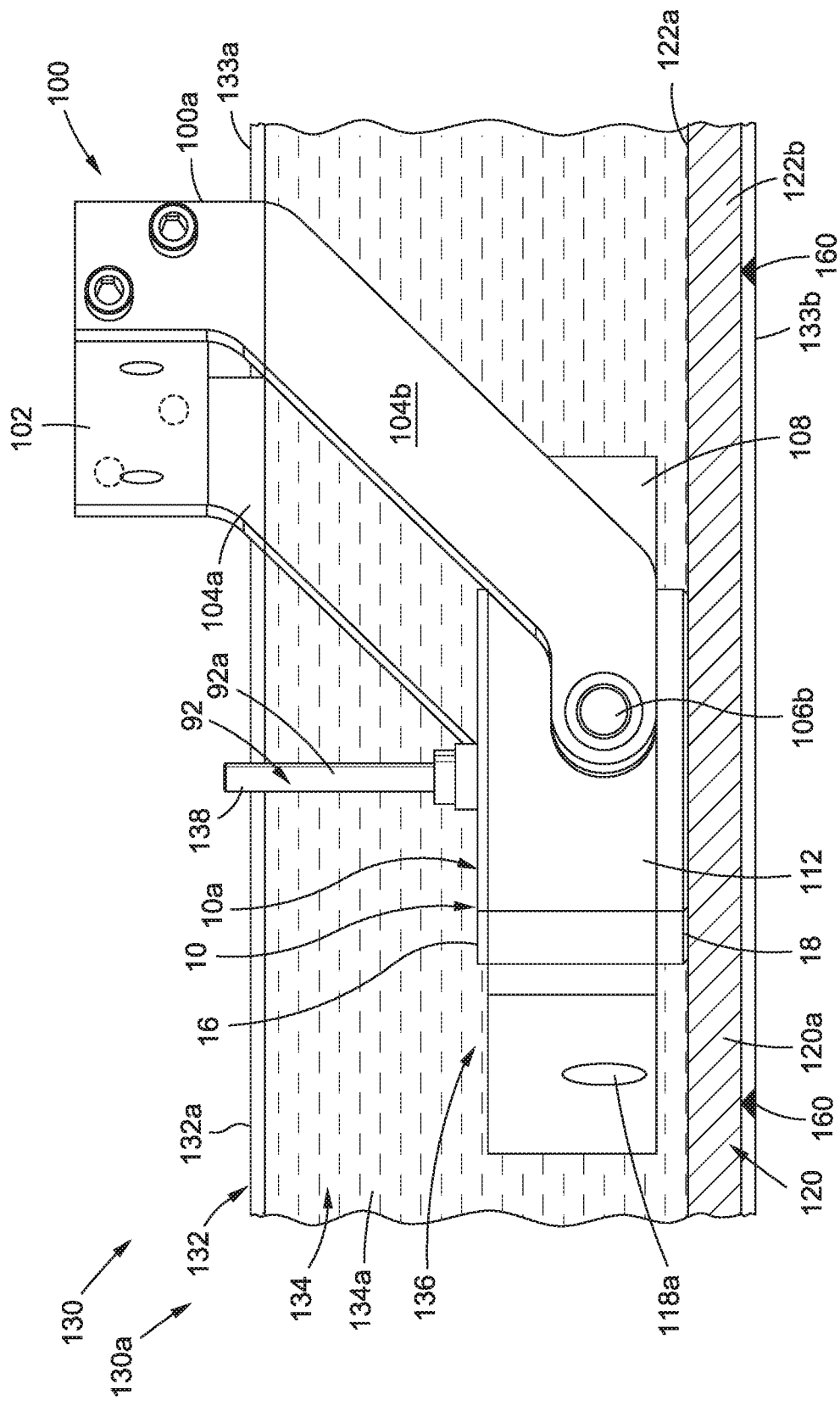
FIG. 3B is an illustration of a side perspective view of the apparatus retaining assembly in the system of FIG. 3A.

Referring now to FIGS. 3A-3B, FIG. 3A is a schematic diagram of an exemplary embodiment of a system 130, such as in the form of an immersion ultrasonic transducer system 130*a*, of the disclosure. FIG. 3B is an illustration of a side perspective view of the apparatus retaining assembly 100 in the system 130 of FIG. 3A.

In another embodiment, there is disclosed the system 130 (see FIGS. 3A-3B), such as in the form of immersion ultrasonic transducer system 130*a* (see FIGS. 3A-B), for removing a gas 142 (see FIG. 3A) in an immersion ultrasonic process 131 (see FIG. 3A). The system 130, such as in the form of immersion ultrasonic transducer system 130*a*, comprises the immersion ultrasonic transducer assembly 90 (see FIGS. 3A-3B) with the apparatus 10 (see FIGS. 3A-3B), such as the immersion ultrasonic transducer holder apparatus 10*a*, and the immersion ultrasonic transducer 92, such as the immersion ultrasonic sensor probe 92*a*.

As shown in FIGS. 3A-3B, the apparatus 10, such as the immersion ultrasonic transducer holder apparatus 10*a*, comprises, as discussed above, the body 12 (see FIG. 3A) with the first end 16, the second end 18, the plurality of sides 20 (see FIG. 3A), the attachment point 26 (see FIG. 3A), and the hollow interior cavity portion 28 (see FIG. 3A). The apparatus 10, such as the immersion ultrasonic transducer holder apparatus 10*a*, of the system 130 (see FIG. 3A) further comprises, as discussed above, the holder portion 40, such as the through opening holder portion 40*a*, formed through the first end 16, and having the exterior end 42*a* and the interior end 42*b*.

As shown in FIG. 3A, the apparatus 10, such as the immersion ultrasonic transducer holder apparatus 10*a*, of the system 130 further comprises, as discussed above, the sloped inner face 70 having the upward sloped surface 74 extending from the base end 71*a* to the evacuation end 71*b*. The knife-edged perimeter 78 (see FIG. 3A) is adjacent the interior end 42*b* (see FIG. 3A) of the holder portion 40 (see FIG. 3A), and the knife-edged perimeter 78 (see FIG. 3A) preferably surrounds the circumference 96*a* (see FIG. 3A) of the transducer face 96 (see FIG. 3A). The apparatus 10, such as in the form of immersion ultrasonic transducer holder apparatus 10*a*, provides a consistent offset distance 80 (see FIG. 1G) between the transducer face 96 (see FIG. 3A) and the structure 120 (see FIG. 3A), during the immersion ultrasonic process 131 (see FIG. 3A).

As shown in FIG. 3A, the apparatus 10, such as the immersion ultrasonic transducer holder apparatus 10*a*, of the system 130 further comprises one or more evacuation ports 50 formed through the first end 16 and located adjacent the evacuation end 71*b* of the sloped inner face 70. The evacuation ports 50 (see FIG. 3A) surround the holder portion 40 (see FIG. 3A) and the immersion ultrasonic transducer 92 (see FIG. 3A), and the evacuation ports 50 are positioned above the transducer face 96.

As shown in FIG. 3A, the system 130, such as in the form of immersion ultrasonic transducer system 130*a*, further comprises one or more immersion ultrasonic transducers 92 positioned in the holder portion 40 of the apparatus 10, such as the immersion ultrasonic transducer holder apparatus 10*a*. The immersion ultrasonic transducer 92 (see FIG. 3A) converts a pulse of electrical energy or a signal transmitted by the immersion ultrasonic transducer 92 (see FIG. 3A) into mechanical energy, in the form of ultrasound waves 140 (see FIG. 3A), that travel through a fluid couplant 134 (see FIG. 3A) to a structure 120 (see FIG. 3A), and through the structure 120 (see FIG. 3A). The ultrasound waves 140 (see FIG. 3A), or returning echoes, reflecting from the structure 120 (see FIG. 3A) are, in turn, converted into signal output 158 (see FIG. 3A), such as pulses of electrical energy or voltage, that may be processed, displayed, and analyzed by a processor and analysis system 154, such as comprising or including one or more computers 156. The ultrasonic waves 140 (see FIG. 3A) are high frequency sound waves and may comprise longitudinal waves (particle motion parallel to wave direction) or shear waves (particle motion perpendicular to wave direction).

As shown in FIG. 3A, the system 130, such as in the form of immersion ultrasonic transducer system 130*a*, further comprises a vessel 132, such as a water tank 132*a*, or another suitable vessel or tank. The vessel 132, such as the water tank 132*a*, comprises a first end 133*a* and a second end 133*b*.

The vessel 132, such as the water tank 132*a*, is filled with a fluid couplant 134 (see FIG. 3A), such as water 134*a* (see FIG. 3A), for example, filtered water, to couple sound energy from the immersion ultrasonic transducer 92 into the structure 120 (see FIG. 3A), such as the part 120*a* (see FIG. 3A). As shown in FIG. 3A, the system 130 may further comprise a fluid delivery system 148 coupled to the vessel 132, via a fluid delivery element 149. The fluid delivery element 149 may comprise a hose, pipe, or other fluid delivery element, for flowing the fluid couplant 134 (see FIG. 3A), such as water 134*a* (see FIG. 3A) into or out of the vessel 132.

The vessel 132 (see FIG. 3A) is configured to hold in the vessel 132 the immersion ultrasonic transducer assembly 90 (see FIG. 3A) comprising the apparatus 10, in the form of the immersion ultrasonic transducer holder apparatus 10*a*, the one or more immersion ultrasonic transducers 92 installed in the apparatus 10, and the apparatus retaining assembly 100. As shown in FIG. 3A, in an immersed position 136, the apparatus 10, in the form of the immersion ultrasonic transducer holder apparatus 10*a*, is fully immersed in the fluid couplant 134, and the immersion ultrasonic transducer 92 installed in the apparatus 10 is partially immersed in the fluid couplant 134. As shown in FIG. 3A, a portion 138 of the immersion ultrasonic transducer 92 is positioned above the fluid couplant 134 and above and out of the vessel 132.

As shown in FIG. 3A, the system 130, such as in the form of immersion ultrasonic transducer system 130*a*, further comprises the apparatus retaining assembly 100, which is configured to retain in the vessel 132 the apparatus 10, such as in the form of immersion ultrasonic transducer holder apparatus 10*a*, with the installed one or more immersion ultrasonic transducers 92, when the one or more immersion ultrasonic transducers 92 scans the structure 120 (see FIG. 3A), during the immersion ultrasonic process 131 (see FIG. 3A). As discussed in detail above, the apparatus retaining assembly 100 preferably comprises a gimbal assembly 100a, having the handle portion 102, arm portions 104a, 104b, pivot pins 106, 106b, and the apparatus enclosure portion 108 with the first end 110a, the second end 110b, the plurality of walls 112, the pivot pin holes 114a, 114b, and the open interior 116.

As shown in FIG. 3A, the system 130 may further comprise a motion control system 150 coupled to the apparatus retaining assembly 100 via a connector element 152. The connector element 152 (see FIG. 3A) may comprise a wired connection, a wireless connection, or other connector device or mechanism. The motion control system 150 may be used to control, on an automated basis, the movement or motion of the apparatus retaining assembly 100, such as in the form of the gimbal assembly 100a.

As shown in FIG. 3A, the system 130, such as in the form of immersion ultrasonic transducer system 130a, may further comprise a processor and analysis system 154 coupled to the one or more immersion ultrasonic transducers 92, and configured to collect, process, display, and analyze signal output 158 received from the one or more immersion ultrasonic transducers 92, during the immersion ultrasonic process 131. The processor and analysis system 154 may include or comprise one or more computers 156 (see FIG. 3A). The processor and analysis system 154 may further comprise known components such as one or more software programs, one or more data collection and recording devices, one or more memory devices, a power source, a controller, one or more connection elements, or other suitable components.

As shown in FIG. 3A, the system 130, such as in the form of immersion ultrasonic transducer system 130a, is designed to perform the immersion ultrasonic process 131, such as an immersion ultrasonic inspection 131a, on the structure 120, such as the part 120a, that is immersed in the fluid couplant 134, such as water 134a, in the vessel 132. The immersion ultrasonic processes 131 (see FIG. 3A) may comprise immersion ultrasonic inspection 131a (see FIG. 3A), or may comprise immersion ultrasonic testing, including but not limited to, on-line or in-process tests on moving parts, scanned tests, optimizing sound coupling into sharp radiuses, grooves, or channels in structures, such as test parts or manufactured parts, with complex geometry, or may comprise other suitable immersion ultrasonic processes.

In the immersion ultrasonic process 131, the structure 120 (see FIG. 3A) is preferably positioned within the vessel 132 (see FIG. 3A) at the second end 133b, and the second surface 122b of the structure 120 (see FIG. 3A) may be elevated or offset from the bottom of the vessel 132 with one or more structure support members 160 (see FIG. 3A). The immersion ultrasonic transducer assembly 90 is positioned on the first surface 122a (see FIG. 3A) of the structure 120, so that the apparatus 10 can ride or move along the first surface 122a, and the immersion ultrasonic transducer 92 can scan the structure 120 and identify any subsurface irregularities 128 (see FIG. 3A), such as subsurface cracks 128b (see FIG. 3A) or other subsurface or surface discontinuities or material features. Alternatively, the structure 120 may be placed on a turntable or roller system, so that the structure 120 may be moved at a constant speed past the immersion ultrasonic transducer 92.

During the immersion ultrasonic process 131 (see FIG. 3A), the apparatus 10, such as the immersion ultrasonic transducer holder apparatus 10a (see FIG. 3A) and the one or more immersion ultrasonic transducers 92 (see FIG. 3A) held in the apparatus 10, such as the immersion ultrasonic transducer holder apparatus 10a (see FIG. 3A), are immersed in the vessel 132 (see FIG. 3A) filled with the fluid couplant 134 (see FIG. 3A), such as water (134a). As shown in FIG. 3, the knife-edged perimeter 78, the sloped inner face 70, and the one or more evacuation ports 50 provide one or more flow paths 144 configured to flow the gas 142 comprising one or more air bubbles 142b, that may be trapped near or on the transducer face 96, away from the transducer face 96, and away from the one or more immersion ultrasonic transducers 92, and flows the air bubbles 142b along the sloped inner face 70, through the one or more evacuation ports 50, and out of the apparatus 10, such as the immersion ultrasonic transducer holder apparatus 10a, thus facilitating flow and removal of the gas 142 (see FIG. 3A).

As shown in FIG. 3A, the flow path 144 may comprise a first flow path 144a where the sharpness of the knife-edged perimeter 78 and the upward sloped surface 74 of the sloped inner face 70 are configured to facilitate flow of gas 142 comprising the air bubbles 142b, that is trapped or caught near or on the transducer face 96, away from the transducer face 96 and away from the one or more immersion ultrasonic transducers 92, and to flow the gas such as the air bubbles 142b upward along the sloped inner face 70. As further shown in FIG. 3A, the flow path 144 may comprise a second flow path 144b, where the vertical configuration of the evacuation ports 50 and the location of the evacuation ports 50 near the evacuation end 71b, facilitate flow of the gas 142 such as the air bubbles 142b upward through the evacuation ports 50 and above the transducer face 96. As further shown in FIG. 3A, the flow path 144 may comprise a third flow path 144c for flowing the gas 142, such as air 142a or air bubbles 142b, out of the apparatus 10, such as the immersion ultrasonic transducer holder apparatus 10a, thus facilitating flow and removal of the gas 142 (see FIG. 3A).

Figure 4:
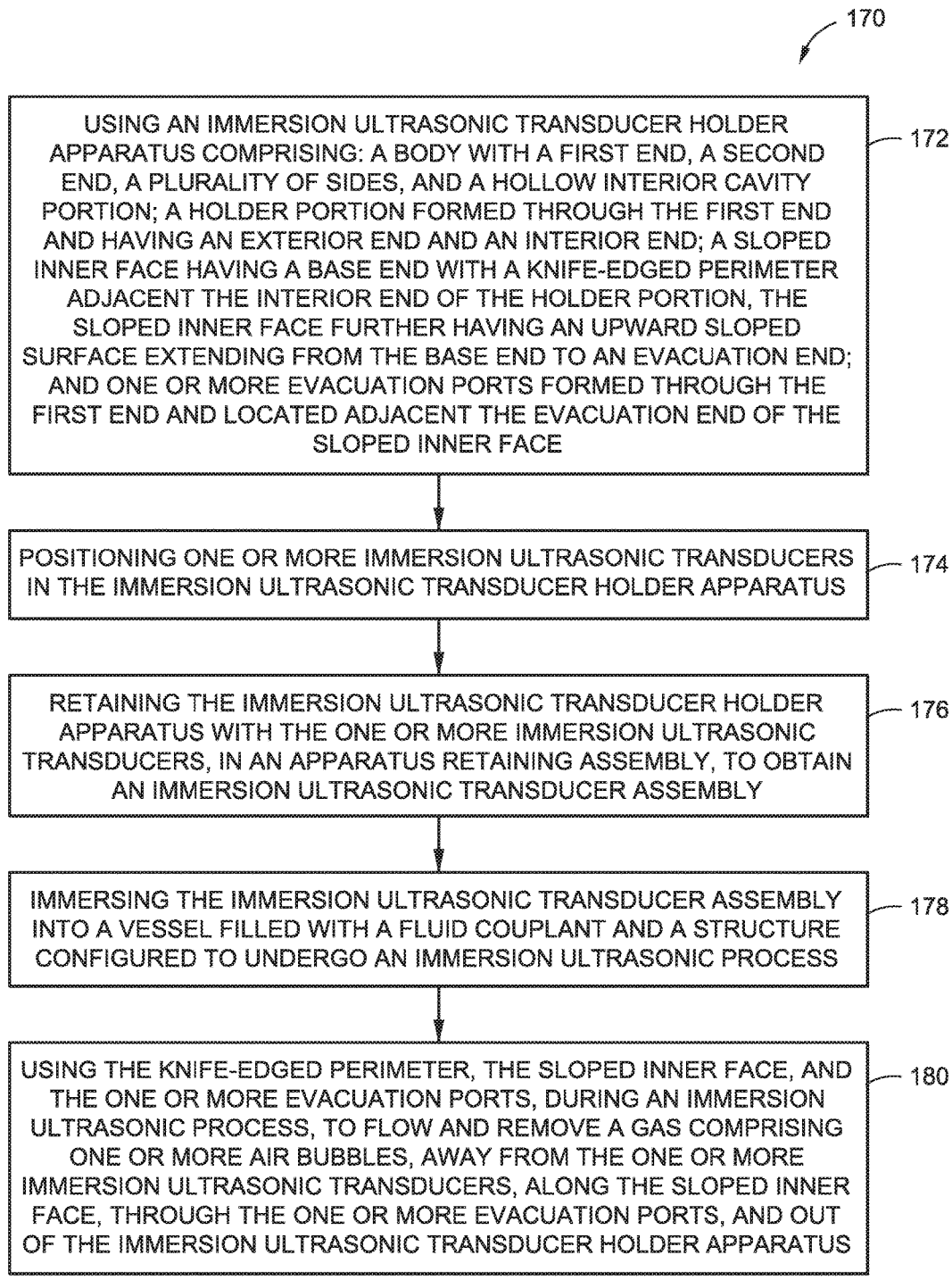
FIG. 4 is an illustration of a flow diagram showing an exemplary method of the disclosure of removing gas in an immersion ultrasonic process.

Referring now to FIG. 4, in another embodiment there is provided a method 170 of removing gas 142 (see FIG. 3A) in an immersion ultrasonic process 131 (see FIG. 3A). FIG. 4 is an illustration of a flow diagram showing the exemplary method 170 of the disclosure.

As shown in FIG. 4, the method 170 comprises step 172 of using an immersion ultrasonic transducer holder apparatus 10a (see FIGS. 1A-1G). As discussed above, the immersion ultrasonic transducer holder apparatus 10a (see FIGS. 1A-1G) comprises a body 12 (see FIG. 1A) with a first end 16 (see FIG. 1A), a second end 18 (see FIG. 1A), a plurality of sides 20 (see FIG. 1A), and a hollow interior cavity portion 28 (see FIG. 1A). The immersion ultrasonic transducer holder apparatus 10a (see FIGS. 1A-1G) further comprises a holder portion 40 (see FIG. 1A) formed through the first end 16 (see FIG. 1A), and having an exterior end 42a (see FIG. 1A) and an interior end 42b (see FIG. 1A).

As discussed above, the immersion ultrasonic transducer holder apparatus 10a (see FIGS. 1A-1G) further comprises a sloped inner face 70 (see FIG. 1G) having a base end 71a (see FIG. 1G) with a knife-edged perimeter 78 (see FIG. 1G) adjacent the interior end 42b (see FIG. 1G) of the holder portion 40 (see FIG. 1G). The sloped inner face 70 (see FIG. 1G) further has an upward sloped surface 74 (see FIG. 1G) extending from the base end 71a (see FIG. 1G) to an evacuation end 71b (see FIG. 1G). The step 172 of using the immersion ultrasonic transducer holder apparatus 10a (see FIG. 1G) may further comprise using the sloped inner face 70 (see FIG. 1G) having a conical-shaped configuration 72 (see FIG. 1G), and an upward sloped surface 74 (see FIG. 1G) sloped at an angle 82 (see FIG. 1G) of from about 20° (twenty degrees) to about 70° (seventy degrees), and preferably, at an angle 82 (see FIG. 1G) of about 30° (thirty degrees). As discussed above, the immersion ultrasonic transducer holder apparatus 10a (see FIGS. 1A-1G) further comprises one or more evacuation ports 50 (see FIG. 1A) formed through the first end 16 (see FIG. 1A) and located adjacent the evacuation end 71b (see FIG. 1A) of the sloped inner face 70 (see FIGS. 1A, 1G).

As shown in FIG. 4, the method 170 further comprises step 174 of positioning one or more immersion ultrasonic transducers 92 (see FIGS. 2A-2B, 3A) in the immersion ultrasonic transducer holder apparatus 10a (see FIGS. 2A-2B). The step 174 (see FIG. 4) of positioning the one or more immersion ultrasonic transducers 92 (see FIG. 2B) in the immersion ultrasonic transducer holder apparatus 10a (see FIG. 2B) may further comprise positioning one immersion ultrasonic transducer 92 (see FIG. 2B) in the immersion ultrasonic transducer holder apparatus 10a (see FIG. 2B), or alternatively, positioning an assembly or array of multiple individual immersion ultrasonic transducers 92 in the immersion ultrasonic transducer holder apparatus 10a. The immersion ultrasonic transducer 92 (see FIG. 2B) has a transducer face 96 (see FIG. 2B), and the knife-edged perimeter 78 (see FIG. 1G) preferably surrounds the circumference 96a (see FIG. 2B) of the transducer face 96 (see FIG. 2B).

As shown in FIG. 4, the method 170 further comprises step 176 of retaining the immersion ultrasonic transducer holder apparatus 10a (see FIGS. 2A-2B) with the one or more immersion ultrasonic transducers 92 (see FIGS. 2A-2B), in an apparatus retaining assembly 100 (see FIGS. 2A-2B), to obtain an immersion ultrasonic transducer assembly 90 (see FIGS. 2A-2B).

As shown in FIG. 4, the method 170 further comprises step 178 of immersing the immersion ultrasonic transducer assembly 90 (see FIGS. 2A, 3A) into a vessel 132 (see FIG. 3A) filled with a fluid couplant 134 (see FIG. 3A), and containing a structure (120) configured to undergo the immersion ultrasonic process (131).

As shown in FIG. 4, the method 170 further comprises step 180 of using the knife-edged perimeter 78 (see FIG. 3A), the sloped inner face 70 (see FIG. 3A), and the one or more evacuation ports 50 (see FIG. 3A), during the immersion ultrasonic process 131 (see FIG. 3A), to flow and remove the gas 142 (see FIG. 3A) comprising one or more air bubbles 142b (see FIG. 3A), away from the one or more immersion ultrasonic transducers 92 (see FIG. 3A) and away from the transducer face 96 (see FIG. 3A), along the sloped inner face 70 (see FIG. 3A), through the one or more evacuation ports 50 (see FIG. 3A), and out of the immersion ultrasonic transducer holder apparatus 10a (see FIG. 3A). The step 180 of using the knife-edged perimeter 78 (see FIG. 3A), the sloped inner face 70 (see FIG. 1G), and the one or more evacuation ports 50 (see FIG. 3A) to flow and remove the gas 142 (see FIG. 3A) comprises flowing and removing the gas 142 (see FIG. 3A) with one of, a manual process, an automated process, or another suitable process.

The method 170 (see FIG. 4) may further comprise coupling the vessel 132 (see FIG. 3A) to a fluid delivery system 148 (see FIG. 3A) via a fluid delivery element 149 (see FIG. 3A), such as a hose, pipe, or other fluid delivery element. The method 170 (see FIG. 4) may further comprise coupling the apparatus retaining assembly 100 (see FIG. 3A) to a motion control system 150 (see FIG. 3A) via a connector element 152 (see FIG. 3A), such as a wired connector element, a wireless connector element, or another suitable connector element. The method 170 (see FIG. 4) may further comprise coupling the one or more immersion ultrasonic transducers 92 (see FIG. 3A) to a processor and analysis system 154 (see FIG. 3A), such as comprising or including one or more computers 156 (see FIG. 3A).

Figure 5:
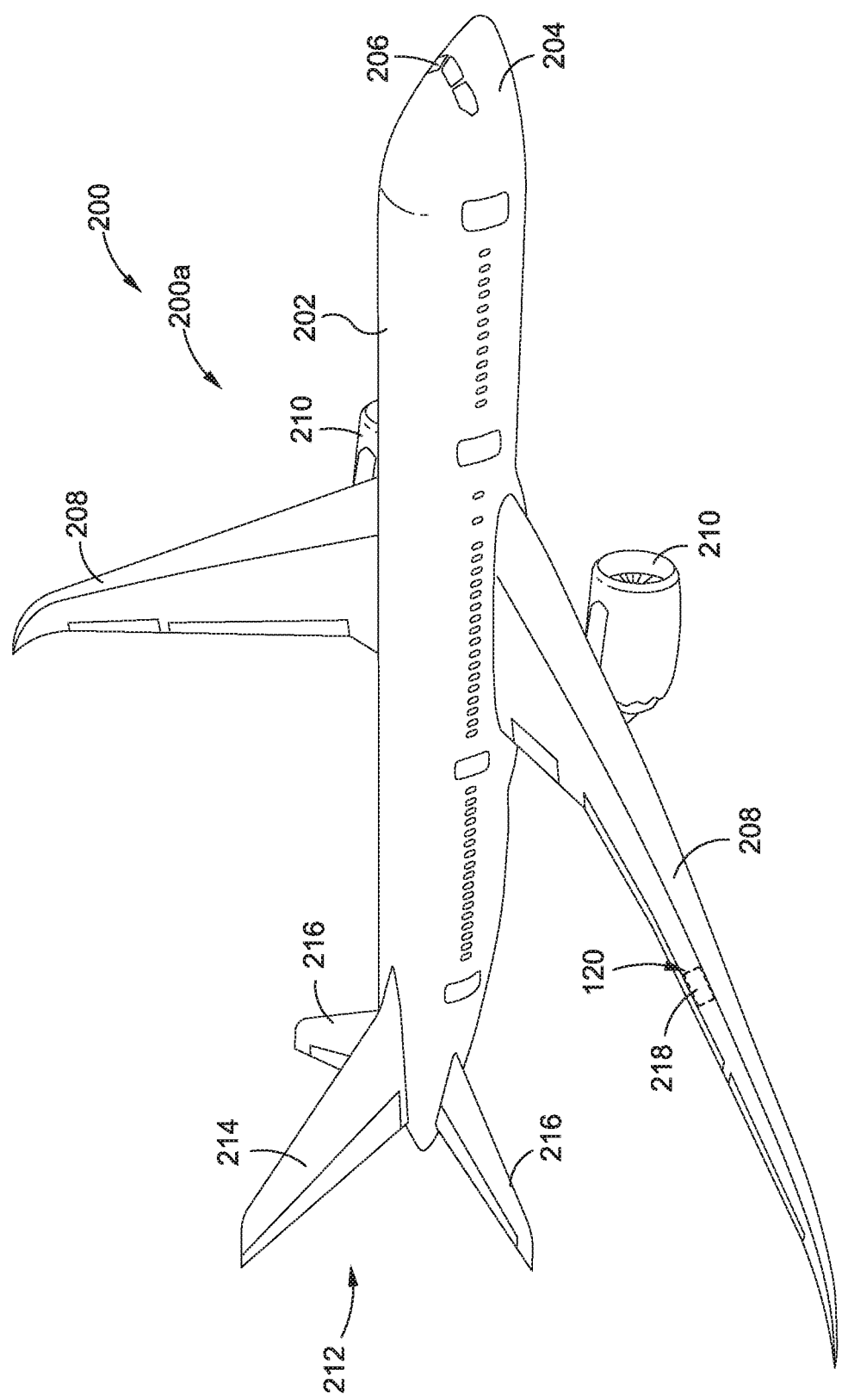
FIG. 5 is an illustration of a perspective view of an air vehicle that incorporates one or more structures that may be inspected or tested with embodiments of the apparatus, system, and method of the disclosure.

Now referring to FIG. 5, FIG. 5 is an illustration of a perspective view of an air vehicle 200, such as an aircraft 200a, that incorporates one or more structures 120, such as an aircraft part 218, that may be inspected or tested with embodiments of the apparatus 10 (see FIGS. 1A-1G), the system 130 (see FIG. 3A), and the method 170 (see FIG. 4) of the disclosure.

As shown in FIG. 5, the air vehicle 200, such as in the form of aircraft 200a, comprises a fuselage 202, a nose 204, a cockpit 206, wings 208, engines 210, and an empennage 212 comprising horizontal stabilizers 214 and a vertical stabilizer 216. As further shown in FIG. 5, the air vehicle 200, such as in the form of aircraft 200a, comprises one or more structures 120, such as one or more aircraft parts 218, installed in the air vehicle 200.

Figure 6:
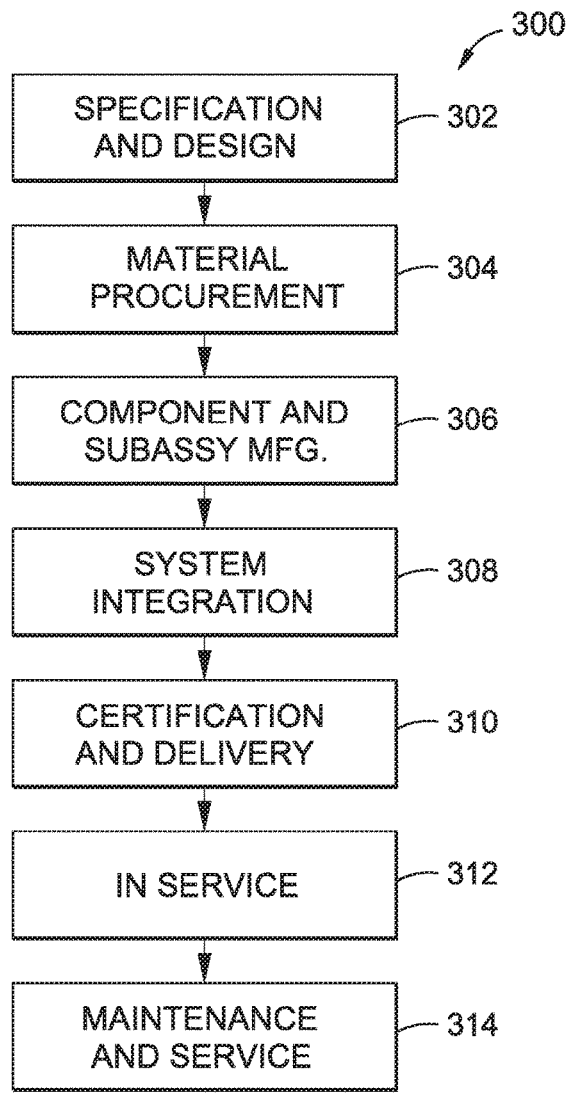
FIG. 6 is an illustration of a flow diagram of an aircraft manufacturing and service method.
Figure 7:
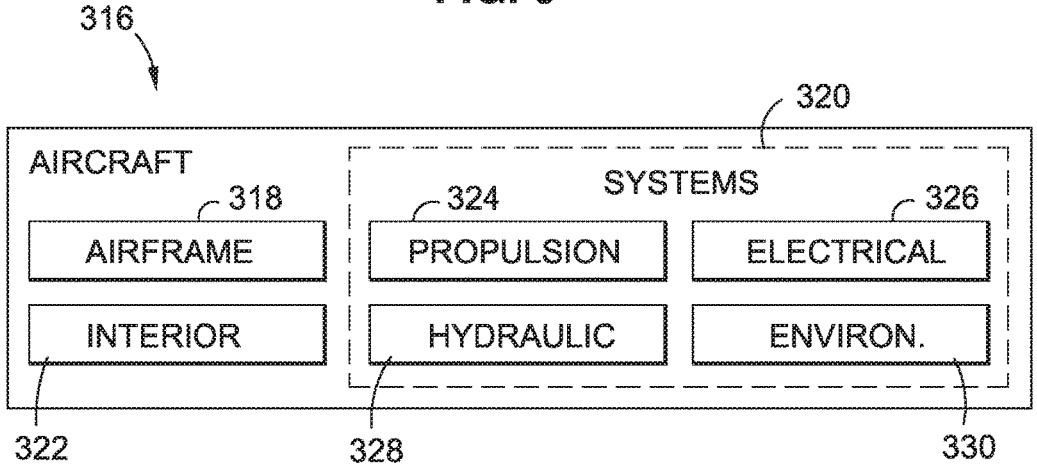
FIG. 7 is an illustration of a block diagram of an aircraft.

FIG. 6 is an illustration of a flow diagram of an aircraft manufacturing and service method 300. FIG. 7 is an illustration of a block diagram of an aircraft 316. Referring to FIGS. 6-7, embodiments of the disclosure may be described in the context of the aircraft manufacturing and service method 300 as shown in FIG. 6, and the aircraft 316 as shown in FIG. 7.

During pre-production, exemplary aircraft manufacturing and service method 300 may include specification and design 302 of the aircraft 316 and material procurement 304. During manufacturing, component and subassembly manufacturing 306 and system integration 308 of the aircraft 316 takes place. Thereafter, the aircraft 316 may go through certification and delivery 310 in order to be placed in service 312. While in service 312 by a customer, the aircraft 316 may be scheduled for routine maintenance and service 314 (which may also include modification, reconfiguration, refurbishment, and other suitable services).

Each of the processes of the aircraft manufacturing and service method 300 may be performed or carried out by a system integrator, a third party, and/or an operator (e.g., a customer). For the purposes of this description, a system integrator may include, without limitation, any number of aircraft manufacturers and major-system subcontractors. A third party may include, without limitation, any number of vendors, subcontractors, and suppliers. An operator may include an airline, leasing company, military entity, service organization, and other suitable operators.

As shown in FIG. 7, the aircraft 316 produced by the exemplary aircraft manufacturing and service method 300 may include an airframe 318 with a plurality of systems 320 and an interior 322. Examples of the plurality of systems 320 may include one or more of a propulsion system 324, an electrical system 326, a hydraulic system 328, and an environmental system 330. Any number of other systems may be included. Although an aerospace example is shown, the principles of the disclosure may be applied to other industries, such as the automotive industry, ship-building industry, and locomotive industry, among others.

Methods and systems embodied herein may be employed during any one or more of the stages of the aircraft manufacturing and service method 300. For example, components or subassemblies corresponding to component and subassembly manufacturing 306 may be fabricated or manufactured in a manner similar to components or subassemblies produced while the aircraft 316 is in service 312. Also, one or more apparatus embodiments, method embodiments, or a combination thereof, may be utilized during component and subassembly manufacturing 306 and system integration 308, for example, by substantially expediting assembly of or reducing the cost of the aircraft 316. Similarly, one or more of apparatus embodiments, method embodiments, or a combination thereof, may be utilized while the aircraft 316 is in service 312, for example and without limitation, to maintenance and service 314.

Disclosed embodiments of the apparatus 10 (see FIGS. 1A-1G), the system 130 (see FIG. 3A), and the method 170 (see FIG. 4), provide a simple to use, low cost, quick, and reliable way to evacuate and remove a gas 142 (see FIG. 3A), such as air 142a (see FIG. 3A), in the form of air bubbles 142b (see FIG. 3A), away from a transducer face 96 (see FIG. 3A) or away from an immersion ultrasonic transducer 92 (see FIG. 3A) during an immersion ultrasonic process 131 (see FIG. 3A). The apparatus 10 (see FIGS. 1A-1G), such as in the form of the immersion ultrasonic transducer holder apparatus 10a (see FIGS. 1A-1G), has the unique features of a knife-edged perimeter 78 (see FIGS. 1G, 3A) that surrounds a circumference 96a (see FIGS. 2B, 3A) of the transducer face 96 (see FIGS. 2B, 3A) of the immersion ultrasonic transducer 92 (see FIGS. 2B, 3A), a sloped inner face 70 (see FIGS. 1G, 3A) with an upward sloped surface 74 (see FIGS. 1G, 3A), and one or more evacuation ports 50 (see FIGS. 1G, 3A) that allow the gas 142 (see FIG. 3A), such as air 142a (see FIG. 3A), in the form of air bubbles 142b (see FIG. 3A), to flow away from the immersion ultrasonic transducer 92 (see FIG. 3A) naturally and easily, without the need for manual manipulation or reorientation of the apparatus 10 upside down, or otherwise, underwater, and without the need for additional equipment, such as vacuum devices or systems, to force the air bubbles out of the apparatus. The apparatus 10 (see FIGS. 1A-1G), the system 130 (see FIG. 3A), and the method 170 (see FIG. 4) thus provide an increased consistency and repeatability of results during testing and inspection in an immersion ultrasonic process 131 (see FIG. 3A), provide a faster and less complex method to remove the gas 142 (see FIG. 3A), such as air 142a (see FIG. 3A), in the form of air bubbles 142b (see FIG. 3A), and provide a decreased expense since no additional equipment to remove the air bubbles is needed.

Moreover, disclosed embodiments of the apparatus 10 (see FIGS. 1A-1G), the system 130 (see FIG. 3A), and the method 170 (see FIG. 4), function immediately after immersion in the fluid couplant 134 (see FIG. 3A), such as water 134a (see FIG. 3A). This may eliminate or minimize any accidental trapped gas 142 (see FIG. 3A), such as air 142a (see FIG. 3A), in the form of air bubbles 142b (see FIG. 3A).

In addition, disclosed embodiments of the apparatus 10 (see FIGS. 1A-1G), the system 130 (see FIG. 3A), and the method 170 (see FIG. 4), provide a design that improves the speed, quality, and repeatability of immersion ultrasonic inspection 131a (see FIG. 3A) and data obtained in the immersion ultrasonic inspection 131a (see FIG. 3A), and improves and increases the removal of gas 142 (see FIG. 3A), such as air 142a (see FIG. 3A), in the form of air bubbles 142b (see FIG. 3A), away from the transducer face 96 (see FIG. 3A) and the away from the immersion ultrasonic transducer 92 (see FIG. 3A). This may result in an improved signal-to-noise ratio, an improved resolution of scans of the structure 120 (see FIG. 3A) by the immersion ultrasonic transducer 92 (see FIG. 3A), and increased data accuracy.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. An apparatus for removing a gas in an immersion ultrasonic process, the apparatus comprising:
   an immersion ultrasonic transducer holder apparatus comprising:
      a body with a first end, a second end, a plurality of sides, and a hollow interior cavity portion;
      a holder portion formed through the first end, and configured to hold one or more immersion ultrasonic transducers in the immersion ultrasonic transducer holder apparatus, the holder portion having an exterior end and an interior end;
      a sloped inner face having a base end with a knife-edged perimeter adjacent the interior end of the holder portion, the sloped inner face further having an upward sloped surface extending from the base end to an evacuation end; and
      one or more evacuation ports formed through the first end and located adjacent the evacuation end of the sloped inner face,
   wherein when the apparatus is used in the immersion ultrasonic process, the knife-edged perimeter, the sloped inner face, and the one or more evacuation ports provide one or more flow paths configured to flow the gas away from the one or more immersion ultrasonic transducers, along the sloped inner face, through the one or more evacuation ports, and out of the apparatus, thus facilitating flow and removal of the gas.

2. The apparatus of claim 1 further comprising two or more attachment points formed through two or more of the plurality of sides, the two or more attachment points configured for attachment to an apparatus retaining assembly comprising a gimbal assembly, when the apparatus is used in the immersion ultrasonic process.

3. The apparatus of claim 1 further comprising one or more fluid evacuation channels, each fluid evacuation channel having an exterior end and an interior end, and each fluid evacuation channel extending through the body, from the interior end intersecting the holder portion, to the exterior end intersecting an exterior of the apparatus.

4. The apparatus of claim 1 wherein the sloped inner face has a conical-shaped configuration, and an upward sloped surface sloped at an angle of from about 20° (twenty degrees) to about 70° (seventy degrees).

5. The apparatus of claim 1 wherein the immersion ultrasonic transducer holder apparatus comprises six evacuation ports surrounding the holder portion.

6. The apparatus of claim 1 wherein the one or more evacuation ports are each vertically oriented, and an evacuation port interior wall of each evacuation port is parallel to a holder portion interior wall of the holder portion.

7. The apparatus of claim 1 wherein the gas comprises air in the form of air bubbles.

8. A system for removing a gas in an immersion ultrasonic process, the system comprising:
   an immersion ultrasonic transducer system comprising:
      an immersion ultrasonic transducer holder apparatus comprising:
         a body with a first end, a second end, a plurality of sides, and a hollow interior cavity portion;
         a holder portion formed through the first end, and having an exterior end and an interior end;

a sloped inner face having a base end with a knife-edged perimeter adjacent the interior end of the holder portion, the sloped inner face further having an upward sloped surface extending from the base end to an evacuation end; and one or more evacuation ports formed through the first end and located adjacent the evacuation end of the sloped inner face;

one or more immersion ultrasonic transducers positioned in the immersion ultrasonic transducer holder apparatus;

a vessel filled with a fluid couplant, the vessel configured to hold in the vessel the immersion ultrasonic transducer holder apparatus with the one or more immersion ultrasonic transducers; and an apparatus retaining assembly configured to retain in the vessel the immersion ultrasonic transducer holder apparatus with the one or more immersion ultrasonic transducers, when the one or more immersion ultrasonic transducers scan a structure during the immersion ultrasonic process, wherein during the immersion ultrasonic process, the immersion ultrasonic transducer holder apparatus and the one or more immersion ultrasonic transducers held in the immersion ultrasonic transducer holder apparatus are immersed in the vessel filled with the fluid couplant, and the knife-edged perimeter, the sloped inner face, and the one or more evacuation ports provide one or more flow paths configured to flow the gas away from the one or more immersion ultrasonic transducers, along the sloped inner face, through the one or more evacuation ports, and out of the immersion ultrasonic transducer holder apparatus, thus facilitating flow and removal of the gas.

9. The system of claim 8 further comprising a fluid delivery system coupled to the vessel via a fluid delivery element.

10. The system of claim 8 further comprising a motion control system coupled to the apparatus retaining assembly via a connector element.

11. The system of claim 8 wherein the gas comprises air in the form of air bubbles.

12. The system of claim 8 further comprising a processor and analysis system coupled to the one or more immersion ultrasonic transducers, and configured to collect, process, display, and analyze signal output received from the one or more immersion ultrasonic transducers during the immersion ultrasonic process.

13. The system of claim 8 wherein the immersion ultrasonic transducer holder apparatus further comprises two or more attachment points formed through two or more of the plurality of sides, the two or more attachment points configured for attachment to the apparatus retaining assembly comprising a gimbal assembly, when the apparatus is used in the immersion ultrasonic process.

14. The system of claim 8 wherein the immersion ultrasonic transducer holder apparatus holds one immersion ultrasonic transducer having a transducer face, and the knife-edged perimeter surrounds a circumference of the transducer face.

15. The system of claim 14 wherein the immersion ultrasonic transducer holder apparatus provides a consistent offset distance between the transducer face and the structure, during the immersion ultrasonic process.

16. A method for removing a gas in an immersion ultrasonic process, the method comprising the steps of:

using an immersion ultrasonic transducer holder apparatus comprising:
a body with a first end, a second end, a plurality of sides, and a hollow interior cavity portion;
a holder portion formed through the first end, and having an exterior end and an interior end;
a sloped inner face having a base end with a knife-edged perimeter adjacent the interior end of the holder portion, the sloped inner face further having an upward sloped surface extending from the base end to an evacuation end; and
one or more evacuation ports formed through the first end and located adjacent the evacuation end of the sloped inner face;

positioning one or more immersion ultrasonic transducers in the immersion ultrasonic transducer holder apparatus;

retaining the immersion ultrasonic transducer holder apparatus with the one or more immersion ultrasonic transducers, in an apparatus retaining assembly, to obtain an immersion ultrasonic transducer assembly;

immersing the immersion ultrasonic transducer assembly into a vessel with a fluid couplant and a structure configured to undergo the immersion ultrasonic process; and using the knife-edged perimeter, the sloped inner face, and the one or more evacuation ports, during the immersion ultrasonic process, to flow and remove the gas away from the one or more immersion ultrasonic transducers, along the sloped inner face, through the one or more evacuation ports, and out of the immersion ultrasonic transducer holder apparatus.

17. The method of claim 16 further comprising coupling the vessel to a fluid delivery system, coupling the apparatus retaining assembly to a motion control system, and coupling the one or more immersion ultrasonic transducers to a processor and analysis system.

18. The method of claim 16 wherein using the immersion ultrasonic transducer holder apparatus comprises using the immersion ultrasonic transducer holder apparatus further comprising two or more attachment points formed through two or more of the plurality of sides, the two or more attachment points configured for attachment to the apparatus retaining assembly comprising a gimbal assembly, when the immersion ultrasonic transducer holder apparatus is used in the immersion ultrasonic process.

19. The method of claim 16 wherein positioning the one or more immersion ultrasonic transducers in the immersion ultrasonic transducer holder apparatus comprises positioning one immersion ultrasonic transducer in the immersion ultrasonic transducer holder apparatus, the immersion ultrasonic transducer having a transducer face, and the knife-edged perimeter surrounding a circumference of the transducer face.

20. The method of claim 16 wherein using the knife-edged perimeter, the sloped inner face, and the one or more evacuation ports to flow and remove the gas comprises flowing and removing the gas comprising air in the form of air bubbles with one of, a manual process and an automated process.

* * * * *